(12) United States Patent
Jones et al.

(10) Patent No.: US 11,363,964 B2
(45) Date of Patent: Jun. 21, 2022

(54) LOCALIZATION SYSTEMS AND METHODS FOR AN INGESTIBLE DEVICE

(71) Applicant: Progenity Inc., San Diego, CA (US)

(72) Inventors: Mitchell Lawrence Jones, La Jolla, CA (US); Yi Liu, Brookline, MA (US); Kate LeeAnn Bechtel, Pleasant Hill, CA (US); Christopher Loren Wahl, La Jolla, CA (US)

( * ) Notice: Subject to any disclaimer, the term of this patent is extended or adjusted under 35 U.S.C. 154(b) by 82 days.

(21) Appl. No.: 15/940,407

(22) Filed: Mar. 29, 2018

(65) Prior Publication Data

US 2018/0279908 A1 Oct. 4, 2018

Related U.S. Application Data

(60) Provisional application No. 62/540,873, filed on Aug. 3, 2017, provisional application No. 62/480,187, filed on Mar. 31, 2017.

(51) Int. Cl.
| | |
|---|---|
| *A61B 5/06* | (2006.01) |
| *A61B 5/00* | (2006.01) |
| *A61B 5/07* | (2006.01) |
| *G16H 40/67* | (2018.01) |
| *A61B 5/11* | (2006.01) |
| *A61B 10/00* | (2006.01) |

(52) U.S. Cl.
CPC ............ *A61B 5/065* (2013.01); *A61B 5/0022* (2013.01); *A61B 5/0071* (2013.01); *A61B 5/0075* (2013.01); *A61B 5/073* (2013.01); *A61B 5/1107* (2013.01); *A61B 5/42* (2013.01); *A61B 5/4839* (2013.01); *A61B 5/6861* (2013.01); *A61B 5/7257* (2013.01); *A61B 10/0045* (2013.01); *A61B 2010/0061* (2013.01); *G16H 40/67* (2018.01)

(58) Field of Classification Search
CPC ......... A61B 5/065; A61B 5/0075; A61B 5/42; A61B 5/073; A61B 5/6861; G16H 40/67
See application file for complete search history.

(56) References Cited

U.S. PATENT DOCUMENTS

| | | | |
|---|---|---|---|
| 3,057,344 | A | 10/1962 | Alberto |
| 3,118,439 | A | 1/1964 | Barana |
| 3,315,660 | A | 4/1967 | Abella |
| 3,485,235 | A | 12/1969 | Felson |
| 4,223,680 | A | 9/1980 | Jobsis |

(Continued)

FOREIGN PATENT DOCUMENTS

| | | |
|---|---|---|
| CN | 1856290 | 11/2006 |
| CN | 101495164 | 7/2009 |

(Continued)

OTHER PUBLICATIONS

Bao et al. 2013 IEEE International Conf. Electro-Information Technol. EIT 2013 pp. 1-5 (Year: 2013).*

(Continued)

*Primary Examiner* — Colin T. Sakamoto
*Assistant Examiner* — Patrick M Mehl
(74) *Attorney, Agent, or Firm* — Procopio Cory Hargreaves and Savitch LLP

(57) ABSTRACT

Ingestible devices are disclosed that provide very high localization accuracy for the devices when present in the GI tract of a body. Related systems and methods are also disclosed.

31 Claims, 15 Drawing Sheets

(56) References Cited

U.S. PATENT DOCUMENTS

| | | | |
|---|---|---|---|
| 4,239,040 A | 12/1980 | Hosoya | |
| 4,292,961 A | 10/1981 | Kawashima | |
| 4,425,117 A | 1/1984 | Hugeman | |
| 4,507,115 A | 3/1985 | Kambara | |
| 4,522,625 A | 6/1985 | Edgren | |
| 4,573,447 A | 3/1986 | Thrash et al. | |
| 4,844,076 A | 7/1989 | Lesho | |
| 5,170,801 A | 12/1992 | Casper | |
| 5,279,607 A | 1/1994 | Schentag | |
| 5,395,366 A | 3/1995 | Andrea | |
| 5,604,531 A | 2/1997 | Iddan et al. | |
| 5,858,001 A | 1/1999 | Tsais et al. | |
| 5,951,538 A | 9/1999 | Joshi | |
| 5,984,860 A | 11/1999 | Shan | |
| 6,082,366 A | 7/2000 | Andra et al. | |
| 6,344,027 B1 | 2/2002 | Goll | |
| 6,428,469 B1 | 8/2002 | Iddan et al. | |
| 6,576,429 B1 | 6/2003 | Hallgren | |
| 6,632,216 B2 | 10/2003 | Houzego | |
| 7,056,673 B2 | 6/2006 | Kamme et al. | |
| 7,553,276 B2 | 6/2009 | Iddan | |
| 7,611,480 B2 | 11/2009 | Levy | |
| 7,797,033 B2 | 9/2010 | D'Andrea et al. | |
| 8,185,185 B2 | 5/2012 | Gilreath | |
| 8,206,285 B2 | 6/2012 | Blijevsky | |
| 8,394,034 B2 | 3/2013 | Iddan | |
| 8,540,623 B2 | 9/2013 | Blijevsky | |
| 8,626,268 B2 | 1/2014 | Adler | |
| 8,696,602 B2 | 4/2014 | Semler et al. | |
| 8,911,368 B2 | 12/2014 | Rabinovitz et al. | |
| 9,026,192 B2 | 5/2015 | Blit et al. | |
| 9,131,842 B2 | 9/2015 | Old | |
| 9,324,145 B1 * | 4/2016 | Cherevatsky | G06T 7/42 |
| 10,588,608 B2 | 3/2020 | Jones et al. | |
| 10,835,152 B2 | 11/2020 | Jones et al. | |
| 2001/0035902 A1 | 11/2001 | Iddan et al. | |
| 2002/0099310 A1 | 7/2002 | Kimchy et al. | |
| 2002/0198470 A1 | 12/2002 | Imran et al. | |
| 2003/0117491 A1 * | 6/2003 | Avni | H04N 5/2354 |
| | | | 348/77 |
| 2003/0139661 A1 | 7/2003 | Kimchy | |
| 2003/0191430 A1 | 10/2003 | Andrea et al. | |
| 2004/0253304 A1 | 12/2004 | Gross et al. | |
| 2004/0254455 A1 | 12/2004 | Iddan | |
| 2005/0010168 A1 | 1/2005 | Kendall | |
| 2005/0049462 A1 | 3/2005 | Kanazawa | |
| 2005/0065441 A1 | 3/2005 | Glukhovsky | |
| 2005/0158246 A1 | 7/2005 | Takizawa | |
| 2005/0266074 A1 | 12/2005 | Zilberstein et al. | |
| 2006/0069317 A1 * | 3/2006 | Horn | A61B 5/065 |
| | | | 600/300 |
| 2006/0178557 A1 | 8/2006 | Mintchev | |
| 2007/0027362 A1 | 2/2007 | Handa | |
| 2007/0043320 A1 | 2/2007 | Kenany | |
| 2007/0092401 A1 | 4/2007 | Liao et al. | |
| 2007/0161928 A1 | 7/2007 | Sprenkels | |
| 2007/0293736 A1 | 12/2007 | Casset | |
| 2008/0027329 A1 | 1/2008 | Glukhovsky | |
| 2008/0051633 A1 * | 2/2008 | Blijevsky | A61B 1/041 |
| | | | 600/117 |
| 2008/0194912 A1 | 8/2008 | Trovato | |
| 2008/0208077 A1 | 8/2008 | Iddan et al. | |
| 2008/0234548 A1 | 9/2008 | Amit | |
| 2008/0294023 A1 | 11/2008 | Rabinovitz et al. | |
| 2009/0131784 A1 | 5/2009 | Betesh | |
| 2010/0045786 A1 | 2/2010 | Kitamura | |
| 2010/0111763 A1 | 5/2010 | Kahn et al. | |
| 2010/0249645 A1 | 9/2010 | Semler et al. | |
| 2010/0285475 A1 | 11/2010 | Palanisanny | |
| 2011/0046458 A1 | 2/2011 | Pinedo | |
| 2011/0125007 A1 | 5/2011 | Steinberg | |
| 2011/0125031 A1 | 5/2011 | Blit et al. | |
| 2011/0274338 A1 * | 11/2011 | Park | A61B 5/4331 |
| | | | 382/133 |
| 2011/0306055 A1 | 12/2011 | Haince | |
| 2011/0313348 A1 | 12/2011 | Potter et al. | |
| 2012/0041465 A1 * | 2/2012 | Shalon | A61B 17/0401 |
| | | | 606/191 |
| 2012/0136209 A1 | 5/2012 | Kostenich et al. | |
| 2012/0258473 A1 | 10/2012 | Moriya et al. | |
| 2013/0013031 A1 | 1/2013 | Ben-Yehuda et al. | |
| 2013/0018279 A1 | 1/2013 | Plante et al. | |
| 2013/0022983 A1 | 1/2013 | Grifantini | |
| 2013/0085414 A1 | 4/2013 | Yamatani | |
| 2013/0158344 A1 | 6/2013 | Taniguchi | |
| 2014/0113313 A1 | 4/2014 | Moreau | |
| 2014/0128833 A1 | 5/2014 | Vogt | |
| 2014/0206956 A1 | 7/2014 | Rabinovitz et al. | |
| 2014/0296666 A1 | 10/2014 | Rabinovitz et al. | |
| 2014/0343451 A1 | 11/2014 | Pannell | |
| 2015/0011874 A1 | 1/2015 | Amoako-Tuffour et al. | |
| 2015/0057548 A1 | 2/2015 | Kaufman | |
| 2016/0007830 A1 * | 1/2016 | Chun | G06T 7/90 |
| | | | 600/476 |
| 2016/0033373 A1 | 2/2016 | Hill et al. | |
| 2016/0038086 A1 | 2/2016 | Wrigglesworth | |
| 2016/0066855 A1 | 3/2016 | Hyde | |
| 2016/0114142 A1 | 4/2016 | Ziaie et al. | |
| 2016/0213234 A1 | 7/2016 | Poon | |
| 2016/0249793 A1 * | 9/2016 | Wang | A61B 1/31 |
| | | | 600/109 |
| 2017/0006202 A1 | 1/2017 | Otani | |
| 2017/0106099 A1 | 4/2017 | Bellinger et al. | |
| 2017/0246438 A1 | 8/2017 | Aran et al. | |
| 2017/0258583 A1 | 9/2017 | McCawley | |
| 2017/0296092 A1 | 10/2017 | Jones et al. | |
| 2018/0049725 A1 | 2/2018 | Jones et al. | |
| 2018/0052084 A1 | 2/2018 | Jones et al. | |
| 2018/0070857 A1 | 3/2018 | Jones et al. | |
| 2018/0160950 A1 | 6/2018 | Rabinovitz et al. | |
| 2020/0245897 A1 | 8/2020 | Jones et al. | |

FOREIGN PATENT DOCUMENTS

| | | | |
|---|---|---|---|
| CN | 103209632 | 7/2013 | |
| CN | 105101863 A | 11/2015 | |
| EP | 108607 | 2/1983 | |
| EP | 1243524 | 9/2002 | |
| EP | 1530950 | 5/2005 | |
| EP | 1932462 | 6/2008 | |
| EP | 2 057 934 | 5/2009 | |
| EP | 3 108 810 | 12/2016 | |
| JP | 2005-73888 | 3/2005 | |
| JP | 2013-500815 | 1/2013 | |
| JP | 2014507982 A | 4/2014 | |
| JP | 2015-509744 | 4/2015 | |
| JP | 2015509744 A | 4/2015 | |
| KR | 100931946 | 12/2009 | |
| RU | 2269343 C1 * | 2/2006 | A61K 31/695 |
| WO | WO 2001045552 | 6/2001 | |
| WO | WO 2010/091926 | 8/2010 | |
| WO | WO 2010/146588 | 12/2010 | |
| WO | WO 2011/016002 | 2/2011 | |
| WO | WO 2013/088444 | 6/2013 | |
| WO | WO 2013120184 | 8/2013 | |
| WO | 2012098798 A | 6/2014 | |
| WO | WO 2015059569 | 4/2015 | |
| WO | WO 2015/099749 | 7/2015 | |
| WO | WO 2015147305 | 10/2015 | |
| WO | 2016049602 A1 | 3/2016 | |
| WO | WO 2016054015 | 4/2016 | |
| WO | WO 2017004000 | 1/2017 | |
| WO | 2015107710 A1 | 3/2018 | |
| WO | WO 2016/049602 | 3/2018 | |
| WO | WO 2018050647 | 3/2018 | |

OTHER PUBLICATIONS

Li et al. 2015 J. Biomed. Opt. 20:121305-1-121305-9 (Year: 2015).*
Mackiewicz et al. 2008 IEEE Trans. Med. Imaging 27:1769-1781 (Year: 2008).*
Lee et al. 2007 Proc. 2007 Meeting ACM-SAC p. 1041-1045 (Year: 2007).*

(56) References Cited

OTHER PUBLICATIONS

Chen et al., "Developing assessment system for wireless capsule endoscopy videos based on event detection", Proceedings of SPIE, vol. 7260, p. 72601G, 2009.
International Search Report and Written Opinion in International Application No. PCT/US2018/025191, dated Oct. 19, 2018.
Lee et al., "Automatic classification of digestive organs in wireless capsule endoscopy videos", Applied Computing 2007. The 22nd Annual ACM Symposium On Applied Computing, 1041-1045, 2007.
Chinese Office Action in Application No. 2015800635638, dated Sep. 29, 2019, 10 pages.
Eurasian Office Action in Application No. 201790706/31, dated May 29, 2019, 4 pages, (with English Translation).
European Exam Report in Application No. 15775911.9, dated Jan. 2, 2020, 4 pages.
Australian Office Action in Application No. 2015319850, dated Aug. 2, 2019, 4 pages.
European Exam Report in Application No. 157759119.9, dated May 28, 2018, 3 pages.
European Exam Report in Application No. 157759119.9, dated Mar. 3, 2019, 4 pages.
Japanese Office Action in Application No. 2017-516962, dated Jul. 22, 2019, 4 pages.
International Search Report and Written Opinion in International Application No. PCT/US2015/052500, dated Dec. 17, 2015, 15 pages.
Invitation to Pay Fees om International Application No. PCT/US2018/025191, Jul. 12, 2018, 22 pages.
Steven L. Jacques, "Optical properties of biological tissues: a review," Phys., Med. Biol., IPEM, 58, R37, 28 pages, 2013.
Anselmo et al., "Non-invasive delivery strategies for biologies", Nature Reviews, Drug Discovery, vol. 18, 19-40, 2019.
Aran et al., "An oral microjet vaccination system elicits antibody production in rabbits", Sci. Transl. Med. 9, eaaf6413,10 pages, 2017.
Barolet et al., "Current trends in needle-free jet injection: an update", Clinical, Cosmetic and Investigational Dermatology, 11, 231-238, 2018.
Battula et al., "A Miniature Shock Wave Driven Micro-Jet Injector for Needle-Free Vaccine/Drug Delivery", Biotechnology and Bioengineering, vol. 113, No. 11, 2507-2512, 2016.
Dingle et al., "Stable and Noncompetitive RNA Internal Control for Routine Clinical Diagnostic Reverse Transcription-PCR", Journal of Clinical Microbiology, vol. 42(3): 1003-1011, Mar. 2004.
Hunter et al., "Aerosol delivery of Virus-like Particles to the genital tract induces local and systemic antibody responses", Vaccine, 29(28): 4584-4592, 2011.
International Search Report and Written Opinion in International Application No. PCT/US2017/050642, dated Jan. 29, 2018, 28 pages.

International Search Report Written Opinion. International Application No. PCT/US2017/047476, dated Jan. 22, 2018, 20 pages.
International Search Report Written Opinion. International Application No. PCT/US2017/047481, dated Jan. 17, 2018, 18 pages.
Invitation to Pay Additional Fees and Where Applicable Protest Fee International Application No. PCT/US2012/047476, dated Nov. 13, 2017, 13 pages.
Invitation to Pay Additional Fees and Where Applicable Protest Fee International Application No. PCT/US2017/050642, dated Dec. 8, 2017, 25 pages.
Invitation to Pay Additional Fees for International Application No. PCT/US2017/047481, dated Nov. 24, 2017, 14 pages.
Iverson et al., "An innate antiviral pathway acting before interferons at epithelial surfaces", Nature Immunology, vol. 17, No. 2, 150-158, 2016.
Kale et al., "Needle free injection technology—An overview", Innovations in pharmacy, vol. 1, No. 1, Article 148, 10 pages, 2014.
Kane et al., "Fecal Lactoferrin Is a Sensitive and Specific Marker in Identifying Intestinal Inflammation", The American Journal of Gastroenterology, 98(6): 1309-1314, 2003.
Kostic et al., "The Gut Microbiome and Disease", Gastroenterology, vol. 146(6): 1489-1499, 2014.
Lambert et al., "Autonomous telemetric capsule to explore the small bowel," Med Biol Eng Comput 29(2): 191-196, 1991.
Lehmann et al.," The role and utility of faecal markers in inflammatory bowel disease", Therapeutic Advances in Gastroenterology, vol. 8(1): 23-36, 2015.
Lo et al., "The use of carbon dioxide in gastrointestinal endoscopy", Gastrointestinal Endoscopy, vol. 83, No. 5, 857-865, 2016.
Sanschagrin and Yergeau, Next-generation Sequencing of 16S Ribosomal RNA Gene Amplicons, Journal of Visualized Experiments, Issue 90: 51709, Aug. 2014.
Sartor and Mazmanian, "Intestinal Microbes in Inflammatory Bowel Diseases", The American Journal of Gastroenterology Supplements, vol. 1, 12-21, 2012.
U.S. Final Office Action in U.S. Appl. No. 15/680,400, dated Jan. 15, 2020, 14 pages.
U.S. Non-Final Office Action in U.S. Appl. No. 15/514,413, dated Mar. 20, 2020, 12 pages.
U.S. Non-Final Office Action in U.S. Appl. No. 15/680,400, dated Mar. 5, 2020, 18 pages.
U.S. Non-Final Office Action in U.S. Appl. No. 15/680,400, dated Oct. 1, 2019, 11 pages.
Wright et al., "Recent Advances in Characterizing the Gastrointestinal Microbiome in Crohn's Disease: A Systematic Review", Inflammatory Bowel Disease Journal, vol. 21(6): 1219-1228, 2015.
EP Extended European Search Report in European Appln. No. 20207295.5, dated Feb. 23, 2021, 7 pages.
Official Action in Japanese patent application No. 2019-553317, dated Nov. 24, 2021.
Office Action in Chinese patent application No. 201880020641.X, dated Jan. 4, 2022.

\* cited by examiner

LOCALIZATION SYSTEMS AND METHODS FOR AN INGESTIBLE DEVICE

CROSS-REFERENCE TO RELATED APPLICATIONS

This application claims priority under 35 U.S.C. § 119 to U.S. Ser. No. 62/480,187, filed Mar. 31, 2017, and entitled "Localization Systems and Methods for an Optoelectromechanical Pill Device," and U.S. Ser. No. 62/540,873, filed Aug. 3, 2017, and entitled "Localization Systems and Methods for an Optoelectromechanical Pill Device." The entire disclosure of each of these applications is incorporated by reference herein.

FIELD

The disclosure relates to ingestible devices and related systems and methods for identifying a location of the ingestible device within a GI tract of a body with relatively high accuracy.

BACKGROUND

The gastrointestinal (GI) tract generally contains a wealth of information regarding an individual's body. For example, contents in the GI tract may provide information regarding the individual's metabolism. An analysis of the contents of the GI tract may also provide information for identifying relationships between the GI content composition (e.g., relationship between bacterial and biochemical contents) and certain diseases or disorders.

SUMMARY

The various embodiments described herein generally relate to devices, systems and methods for determining the location of an ingestible device within a GI tract of a subject. The devices, systems and methods can yield highly reliable data for determining the location of an ingestible device within the GI tract of a subject. Optionally, the devices can use this information to locally treat a condition in the GI tract.

In one general aspect, the disclosure provides an ingestible device that includes one or more processing devices, and one more machine readable hardware storage devices storing instructions that are executable by the one or more processing devices to determine a location of the ingestible device in a portion of a GI tract of a subject to an accuracy of at least 85%, e.g., at least 90%, at least 95%, at least 97%, at least 98%, at least 99%, 100%. The portion of the portion of the GI tract of the subject can include, for example, the duodenum, the jejunum, and/or the terminal ileum, cecum and colon.

In one general aspect, the disclosure provides an ingestible device that includes one or more processing devices, and one more machine readable hardware storage devices storing instructions that are executable by the one or more processing devices to determine that the ingestible device is in the cecum of a subject to an accuracy of at least 70%, e.g., at least 75%, at least 80%, at least 85%, at least 88%, at least 89%.

In one general aspect, the disclosure provides an ingestible device that includes one or more processing devices, and one more machine readable hardware storage devices storing instructions that are executable by the one or more processing devices to transmit data to a device capable of implementing the data to determine a location of the medical device in a portion of a GI tract of a subject to an accuracy of at least 85%, e.g., at least 90%, at least 95%, at least 97%, at least 98%, at least 99%, 100%. The portion of the GI tract can include, for example, the duodenum, the jejunum, and/or the terminal ileum, cecum and colon.

In one general aspect, the disclosure provides an ingestible device that includes one or more processing devices, and one more machine readable hardware storage devices storing instructions that are executable by the one or more processing devices to transmit data to an external device capable of implementing the data to determine that the ingestible device is in the cecum of a subject to an accuracy of at least 70%, e.g., at least 75%, at least 80%, at least 85%, at least 88%, at least 89%.

In some embodiments, an ingestible device further includes first and second light sources, wherein the first light source is configured to emit light at a first wavelength, and the second light source is configured to emit light at a second wavelength different from the first wavelength.

In some embodiments, an ingestible device further includes first and second detectors, wherein the first detector is configured to detect light at the first wavelength, and the second detector is configured to detect light at the second wavelength.

In some embodiments, the data include intensity data for at least two different wavelengths of light.

In one general aspect, the disclosure provides a method that includes determining a location of the ingestible medical device in a portion of a GI tract of a subject to an accuracy of at least 85%, e.g., at least 90%, at least 95%, at least 97%, at least 98%, at least 99%, 100%. The portion of the GI tract can include, for example, the duodenum, the jejunum, and/or the terminal ileum, cecum and colon.

In one general aspect, the disclosure provides a method that includes determining a location of an ingestible medical device within the GI tract of a subject based on measured reflected light signals within the GI tract, wherein the reflected signals include light of at least two different wavelengths.

In one general aspect, the disclosure provides a method that includes determining a location of an ingestible medical device within the GI tract of a subject based on measured reflected light signals within the GI tract, wherein the reflected signals comprise light of at least two different wavelengths.

In some embodiments, a method includes determining the location of the ingestible device within the GI tract of a subject includes determining reflected light signals within the GI tract, wherein the reflected signals comprise light of at least two different wavelengths. The reflected signals can include light of at least three different wavelengths. For example, the reflected light can include first and second wavelengths, wherein the first wavelength is between 495-600 nm, and the second wavelength is between 400-495 nm. Optionally, the first and second wavelengths are separated by at least 50 nm.

In some embodiments, the reflected signals can include light of at least three different wavelengths. The wavelengths can include a first wavelength between 495-600 nm and a second wavelength between 400-495 nm. Optionally, the first and second wavelengths are separated by at least 50 nm.

In some aspects, a method for determining a location of an ingestible device within a gastrointestinal tract of a body is provided herein. The method comprises transmitting a first illumination at a first wavelength and a second illumination at a second wavelength towards an environment external to a housing of the ingestible device; detecting a first reflectance from the environment resulting from the first illumination and a second reflectance from the environment resulting from the second illumination, wherein the first reflectance value is indicative of an amount of light in the first reflectance, and the second reflectance value is indicative of an amount of light in the second reflectance; storing a ratio of the first reflectance value and the second reflectance value in a data set, the data set including a plurality of values, each of the plurality of values corresponding to a respective ratio of a respective first reflectance and a respective second reflectance detected at a respective time; obtaining, from the data set, a first subset of values, the first subset of values corresponding to a first predetermined number of recent measurements; obtaining, from the data set, a second subset of values, the second subset of values corresponding to a second predetermined number of past measurements, the recent measurements being taken at a recent time range that is separated from a past time range when the past measurements were taken by at least a predetermined period of time; and identifying a change in the location of the ingestible device within the gastrointestinal tract of the body when a difference between a first mean value of the first subset of values and a second mean value of the second subset of values exceeds a threshold value.

In at least some embodiments, the first wavelength may be in approximately the green spectrum of light between 495-600 nm and the second wavelength may be in approximately the blue spectrum of light between 400-495 nm, and the first wavelength and the second wavelength are separated by at least 50 nm.

In at least some embodiments, the retrieval of the first subset of values and the retrieval of the second subset of values includes obtaining a first raw subset of values by applying a first sliding window filter to the data set; obtaining a second raw subset of values by applying a second sliding window filter to the data set; determining the first subset of values by removing a first set of outliers from the first raw subset of values, the first set of outliers being identified based on a standard deviation of the first raw subset of values; and determining the second subset of values by removing a second set of outliers from the second raw subset of values, the second set of outliers being identified based on a standard deviation of the second raw subset of values.

In at least some embodiments, the first sliding window filter and the second sliding window filter are each configured to select a number of values from the data set, the number being between ten and forty.

In at least some embodiments, the first sliding window filter and the second sliding window filter are each configured to select a predetermined range of data values from the data set, the predetermined range of data values being between fifteen seconds of data and five minutes of data.

In at least some embodiments, the predetermined period of time is within a range that is substantially similar to one to five times the predetermined range of data values.

In at least some embodiments, the threshold value is based on a standard deviation of at least one of the first subset of values and the second subset of values.

In at least some embodiments, the identification of the change in the location of the ingestible device includes determining that a preceding location of the ingestible device was a stomach; and storing data indicative of a detected pyloric transition from the stomach to a duodenum in response to determining that the first mean value of the first subset of values is greater than the second mean value of the second subset of values by greater than three times a standard deviation of the second subset of values.

In at least some embodiments, the storage of the data indicative of the detected pyloric transition includes storing data indicative of the second mean value of the second subset of values as an average signal level in the stomach in response to determining that there was no previously stored data indicative of the detected pyloric transition.

In at least some embodiments, the storage of the data indicative of the detected pyloric transition includes retrieving data indicative of an average signal level in the stomach; and storing the data indicative of the detected pyloric transition in response to further determining that the first mean value of the first subset of values is greater than a predetermined multiple of the average signal level in the stomach, the predetermined multiple being greater than 1.2.

In at least some embodiments, the identification of the change in the location of the ingestible device includes determining that a preceding location of the ingestible device was a duodenum; retrieving data indicative of an average signal level in the stomach; and storing data indicative of a detected reverse pyloric transition from the duodenum to a stomach in response to determining that the first mean value of the first subset of values is less than a predetermined multiple of the average signal level in the stomach, the predetermined multiple being greater than 1.2.

In some embodiments, another ingestible device is provided herein. The ingestible device includes a housing defined by a first end, a second end opposite from the first end, and a radial wall extending longitudinally from the first end to the second end; a sensing sub-unit configured to: transmit a first illumination at a first wavelength and a second illumination at a second wavelength towards an environment external to a housing of the ingestible device; and detect a first reflectance from the environment resulting from the first illumination and a second reflectance from the environment resulting from the second illumination, wherein the first reflectance value is indicative of an amount of light in the first reflectance, and the second reflectance value is indicative of an amount of light in the second reflectance; and a processing unit located within the ingestible device configured to: store a ratio of the first reflectance value and the second reflectance value in a data set, the data set including a plurality of values, each of the plurality of values corresponding to a respective ratio of a respective first reflectance and a respective second reflectance detected at a respective time; obtain, from the data set, a first subset of values, the first subset of values corresponding to a first predetermined number of recent measurements; obtain, from the data set, a second subset of values, the second subset of values corresponding to a second predetermined number of past measurements, the recent measurements being taken at a recent time range that is separated from a past time range when the past measurements were taken by at least a predetermined period of time; and identify a change in the location of the ingestible device within the gastrointestinal tract of the body when a difference between a first mean value of the first subset of values and a second mean value of the second subset of values exceeds a threshold value.

In some embodiments, the ingestible device may be further defined according to any one of the teaching herein.

In some aspects a method for determining a location of an ingestible device within a gastrointestinal tract of a body based on peristaltic motion is described herein. The method includes periodically transmitting an illumination towards an environment external to a housing of the ingestible device at a plurality of different times, each of the plurality of different times being separated by a periodic interval; detecting a plurality of reflectances from the environment resulting from the illumination transmitted at the plurality of different times; obtaining and storing a plurality of reflectance values in a data set, wherein each of the plurality of reflectance values is indicative of an amount of light in a respective reflectance of the plurality of reflectances detected from a respective illumination transmitted at a respective time; calculating a frequency spectrum based on the data set; and identifying a change in the location of the ingestible device within the gastrointestinal tract of the body when at least a portion of the frequency spectrum between a predetermined frequency range exceeds a threshold value.

In at least some embodiments, the periodic interval is between 0.1 seconds and 3.0 seconds, the frequency spectrum is a normalized frequency spectrum, the predetermined frequency range is 0.05 Hz to 0.33 Hz, and the threshold value is greater than or equal to 0.5.

In at least some embodiments, the periodic transmission of the illumination includes detecting a pyloric transition from a stomach to a duodenum; and initiating the periodic transmission of the illumination in response to detecting the pyloric transition.

In at least some embodiments, the illumination comprises light of a wavelength between 300 nm and 2500 nm.

In at least some embodiments, the calculation of the frequency spectrum includes obtaining a first subset of data by applying a window filter to the data set; obtaining a second subset of data comprising data points for at least every 0.5 seconds by interpolating the first subset of data; and calculating the frequency spectrum by applying a Fourier transform procedure to the second subset of data.

In at least some embodiments, the identification of the change in the location of the ingestible device includes determining that a proceeding location of the ingestible device was a duodenum; and storing data indicative of a detected transition from the duodenum to a jejunum in response to determining that the at least the portion of the frequency spectrum between 0.05 Hz and 0.33 Hz exceeds the threshold value.

In at least some embodiments, the storage of data indicative of the detected transition from the duodenum to the jejunum includes storing data indicative of a detected muscle contraction in response to determining that the at least the portion of the frequency spectrum between 0.05 Hz and 0.33 Hz exceeds the threshold value; retrieving data indicative of a total number of detected muscle contractions; and storing the data indicative of the detected transition from the duodenum to the jejunum in response to further determining that a total number of detected muscle contractions exceeds a predetermined threshold number of detected muscle contractions.

In at least some embodiments, the illumination is a first illumination at a first wavelength, the plurality of reflectances are a first plurality of reflectances, the plurality of reflectance values are a first plurality of reflectance values, the data set is a first data set, the frequency spectrum is a first frequency spectrum, and further includes periodically transmitting a second illumination at a second wavelength towards the environment external to the housing of the ingestible device at the plurality of different times; obtaining and storing a second plurality of reflectance values in a second data set, wherein each of the second plurality of reflectance values is indicative of an amount of light in a respective reflectance of the second plurality of reflectances detected from a respective second illumination; calculating a second frequency spectrum based on the second data set; and identifying the change in the location of the ingestible device within the gastrointestinal tract of the body by detecting when at least a portion of either the first frequency spectrum or the second frequency spectrum between 0.05 Hz and 0.33 Hz exceeds a threshold value.

In at least some embodiments, the method comprises: obtaining a fluid sample from the environment external to a housing of the ingestible device in response to identifying the change in the location of the ingestible device.

In at least some embodiments, the method comprises: delivering a dispensable substance that is pre-stored within the ingestible device from the ingestible device into the gastrointestinal tract in response to identifying the change in the location of the ingestible device.

In at least some embodiments, the method comprises: retrieving data indicative of a total number of detected muscle contractions; comparing a total number of detected muscle contractions to a total number of expected muscle contractions from a healthy individual; and performing an action in response to the determining, the action comprising at least one of: obtaining a fluid sample from the environment external to a housing of the ingestible device; and delivering a dispensable substance that is pre-stored within the ingestible device from the ingestible device into the gastrointestinal tract.

In some embodiments, another ingestible device is provided herein. The ingestible device includes a housing defined by a first end, a second end opposite from the first end, and a radial wall extending longitudinally from the first end to the second end; a sensing sub-unit configured to: transmit a first illumination at a first wavelength and a second illumination at a second wavelength towards an environment external to a housing of the ingestible device; and detect a first reflectance from the environment resulting from the first illumination and a second reflectance from the environment resulting from the second illumination, wherein the first reflectance value is indicative of an amount of light in the first reflectance, and the second reflectance value is indicative of an amount of light in the second reflectance; and a processing unit located within the ingestible device configured to: store a ratio of the first reflectance value and the second reflectance value in a data set, the data set including a plurality of values, each of the plurality of values corresponding to a respective ratio of a respective first reflectance and a respective second reflectance detected at a respective time; obtain, from the data set, a first subset of values, the first subset of values corresponding to a first predetermined number of recent measurements; obtain, from the data set, a second subset of values, the second subset of values corresponding to a second predetermined number of past measurements, the recent measurements being taken at a recent time range that is separated from a past time range when the past measurements were taken by at least a predetermined period of time; and identify a change in the location of the ingestible device within the gastrointestinal tract of the body when a difference between a first mean value of the first subset of values and a second mean value of the second subset of values exceeds a threshold value.

In some embodiments, the ingestible device may be further defined according to any one of the teaching herein.

In a general aspect, the disclosure provides a networked system that includes: an ingestible device that generates device data, with at least a portion of the device data representing a location of the ingestible device in a portion of a GI tract of a subject to an accuracy of at least 85%; a receiver that receives, from the ingestible device and over one or more networks, the device data; a mobile device that receives, from the receiver, the device data and transmits, over one more networks, the device data to one or more hardware storage devices; and a data analytics system that retrieves the device data from the one or more hardware storage devices and processes the device data to generate analytics data.

In a general aspect, the disclosure provides a networked system that includes: an ingestible device that generates device data, with at least a portion of the device data representing that the ingestible device is in the cecum of a subject to an accuracy of at least 70%; a receiver that receives, from the ingestible device and over one or more networks, the device data; a mobile device that receives, from the receiver, the device data and transmits, over one more networks, the device data to one or more hardware storage devices; and a data analytics system that retrieves the device data from the one or more hardware storage devices and processes the device data to generate analytics data.

In a general aspect, the disclosure provides a networked system that includes: an ingestible device that generates device data; a networked receiver that receives the device data and causes determination, in accordance with the device data, of a location of the ingestible device in a portion of a GI tract of a subject to an accuracy of at least 85%; a mobile device that receives, from the networked receiver, data and transmits, over one more networks, the received data to one or more hardware storage devices; and a data analytics system that retrieves the received data from the one or more hardware storage devices and processes the received data to generate analytics data.

In a general aspect, the disclosure provides a networked system that includes: an ingestible device that generates device data; a networked receiver that receives the device data and causes determination, in accordance with the device data, that the ingestible device is in the cecum of subject to an accuracy of at least 70%; a mobile device that receives, from the networked receiver, data and transmits, over one more networks, the received data to one or more hardware storage devices; and a data analytics system that retrieves the received data from the one or more hardware storage devices and processes the received data to generate analytics data.

In a general aspect, the disclosure provides a computer-implemented method that includes: receiving, from an ingestible device, device data specifying a location of the ingestible device in a portion of a GI tract of a subject to an accuracy of at least 85%; and executing executable logic against the received device data to generate analytics data specifying one or more decision support recommendations.

In a general aspect, the disclosure provides a computer-implemented method that includes: receiving, from an ingestible device, device data specifying that the ingestible device is in the cecum of a subject to an accuracy of at least 70%; and executing executable logic against the received device data to generate analytics data specifying one or more decision support recommendations.

In a general aspect, the disclosure provides a computer-implemented method that includes: receiving, from an ingestible device, data; and determining, based on the received data and by a device that is external to the ingestible device, a location of the ingestible device in a portion of a GI tract of a subject to an accuracy of at least 85%.

In a general aspect, the disclosure provides a computer-implemented method that includes: receiving, from an ingestible device, data; and determining, based on the received data and by a device that is external to the ingestible device, that the ingestible device is in the cecum of a subject to an accuracy of at least 70%.

In a general aspect, the disclosure provides a computer-implemented method that includes: receiving, from an ingestible device, device data specifying a location of the ingestible device within the GI tract of a subject based on measured reflected light signals within the GI tract, wherein the reflected signals comprise light of at least two different wavelengths; and executing executable logic against the received device data to generate analytics data specifying one or more decision support recommendations.

It should be noted that the systems and/or methods described above may be applied to, or used in accordance with, other system, methods, and/or apparatuses.

BRIEF DESCRIPTION OF THE DRAWINGS

The above and other objects and advantages will become apparent with consideration of the following detailed description, taken in conjunction with the accompanying drawings, in which like reference characters refer to like parts throughout, and in which.

DESCRIPTION OF EXEMPLARY EMBODIMENTS

Figure 1:
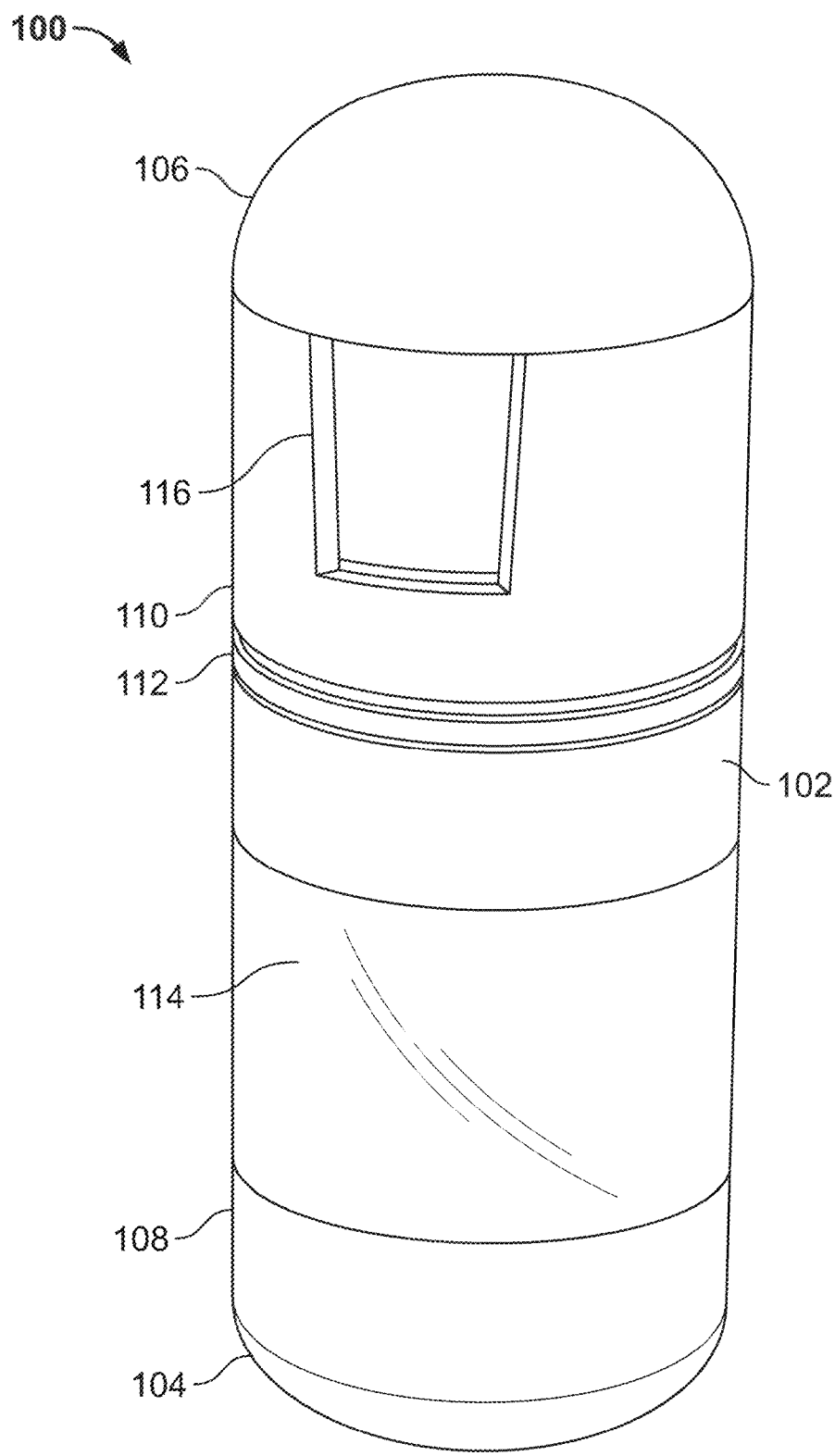
FIG. 1 is a view of an example embodiment of an ingestible device, in accordance with some embodiments of the disclosure.

This application incorporates by reference the following patent applications: U.S. Ser. No. 14/460,893, filed Aug. 15, 2014, and entitled "Ingestible Medical Device;" U.S. Ser. No. 15/514,413, filed Mar. 24, 2017, and entitled "Electromechanical Pill Device with Localization Capabilities;" U.S. Ser. No. 15/680,400, filed Aug. 18, 2017, and entitled "Systems and Methods for Obtaining Samples using Ingestible Devices;" U.S. Ser. No. 15/699,848, filed Sep. 8, 2017, and entitled "Electromechanical Ingestible Device for Delivery of a Dispensable Substance'; and U.S. Ser. No. 62/642,544, filed Mar. 13, 2018, and entitled "Ingestible Device with Relatively Large Payload Volume." The entire contents of each of these applications is incorporated by reference herein.

Various systems, devices, and methods are described herein to provide an example of at least one embodiment for the claimed subject matter. No embodiment limits any claimed subject matter and any claimed subject matter may cover systems, devices, and methods that differ from those described herein. It is possible that the claimed subject matter are not limited to systems, devices, and methods having all of the features of any one of the systems, devices, and methods described herein or to features common to multiple or all of the systems, devices, and methods described herein. It may be possible that a system, device, or method described herein is not an embodiment of any claimed subject matter. Any subject matter disclosed in systems, devices, and methods described herein that is not claimed in this document may be the subject matter of another protective instrument, for example, a continuing or divisional patent application, and the applicants, inventors or owners do not intend to abandon, disclaim or dedicate to the public any such subject matter by its disclosure in this document.

It will be appreciated that, for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should be noted that terms of degree such as "substantially," "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive- or. That is, "X and/or Y" is intended to mean X or Y or both, for example. As a further example, "X, Y, and/or Z" is intended to mean X or Y or Z or any combination thereof.

The various embodiments described herein generally relate to an ingestible device for identifying one or more locations within the gastrointestinal (GI) tract and, in some embodiments, for collecting data and/or releasing substances including medicaments and therapeutics at the identified location. As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Referring now to FIG. 1, shown therein is a view of an example embodiment of an ingestible device 100, which may be used to identify a location within a gastrointestinal (GI) tract. In some embodiments, ingestible device 100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 100 may be configured to autonomously determine whether it is located within certain portions of the small intestine or large intestine, such as the duodenum, the jejunum, the cecum, or the colon.

Ingestible device 100 may have a housing 102 shaped similar to a pill or capsule. The housing 102 of ingestible device 100 may have a first end portion 104, and a second end portion 106. The first end portion 104 may include a first wall portion 108, and second end portion 106 may include a second wall portion 110. In some embodiments, first end portion 104 and second end portion 106 of ingestible device 100 may be manufactured separately, and may be affixed together by a connecting portion 112.

In some embodiments, ingestible device 100 may include an optically transparent window 114. Optically transparent window 114 may be transparent to various types of illumination in the visible spectrum, infrared spectrum, or ultraviolet light spectrum, and ingestible device 100 may have various sensors and illuminators located within the housing 102, and behind the transparent window 114. This may allow ingestible device 100 to be configured to transmit illumination at different wavelengths through transparent window 114 to an environment external to housing 102 of ingestible device 100, and to detect a reflectance from a portion of the illumination that is reflected back through transparent window 114 from the environment external to housing 102. Ingestible device 100 may then use the detected level of reflectance in order to determine a location of ingestible device 100 within a GI tract. In some embodiments, optically transparent window 114 may be of any shape and size, and may wrap around the circumference of ingestible device 100. In this case, ingestible device 100 may have multiple sets of sensors and illuminators positioned at different locations azimuthally behind window 114.

In some embodiments, ingestible device 100 may optionally include an opening 116 in the second wall portion 110. In some embodiments, the second wall portion 110 may be configured to rotate around the longitudinal axis of ingestible device 100 (e.g., by means of a suitable motor or other actuator housed within ingestible device 100). This may allow ingestible device 100 to obtain a fluid sample from the GI tract, or release a substance into the GI tract, through opening 116.

Figure 2:
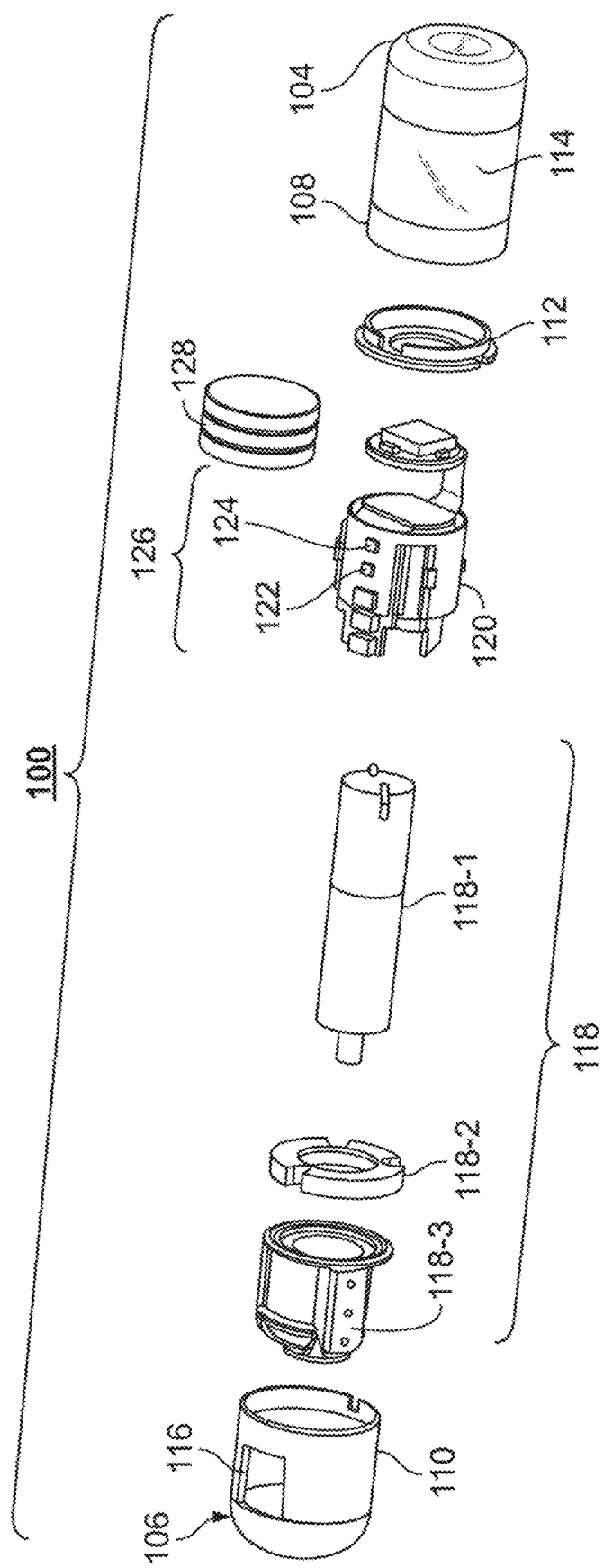
FIG. 2 is an exploded view of the ingestible device of FIG. 1, in accordance with some embodiments of the disclosure.

FIG. 2 shows an exploded view of ingestible device 100. In some embodiments, ingestible device 100 may optionally include a rotation assembly 118. Optional rotation assembly 118 may include a motor 118-1 driven by a microcontroller (e.g., a microcontroller coupled to printed circuit board 120), a rotation position sensing ring 118-2, and a storage sub-unit 118-3 configured to fit snugly within the second end portion 104. In some embodiments, rotation assembly 118 may cause second end portion 104, and opening 116, to rotate relative to the storage sub-unit 118-3. In some embodiments, there may be cavities on the side of storage sub-unit 118-3 that function as storage chambers. When the opening 116 is aligned with a cavity on the side of the storage sub-unit 118-3, the cavity on the side of the storage sub-unit 118-3 may be exposed to the environment external to the housing 102 of ingestible device 100. In some embodiments, the storage sub-unit 118-3 may be loaded with a medicament or other substance prior to the ingestible device 100 being administered to a subject. In this case, the medicament or other substance may be released from the ingestible device 100 by aligning opening 116 with the cavity within storage sub-unit 118-3. In some embodiments, the storage sub-unit 118-3 may be configured to hold a fluid sample obtained from the GI tract. For example, ingestible device 100 may be configured to align opening 116 with the cavity within storage sub-unit 118-3, thus allowing a fluid sample from the GI tract to enter the cavity within storage sub-unit 118-3. Afterwards, ingestible device 100 may be configured to seal the fluid sample within storage sub-unit 118-3 by further rotating the second end portion 106 relative to storage sub-unit 118-3. In some embodiments, storage sub-unit 118-3 may also contain a hydrophilic sponge, which may enable ingestible device 100 to better draw certain types of fluid samples into ingestible device 100. In some embodiments, ingestible device 100 may be configured to either obtain a sample from within the GI tract, or to release a substance into the GI tract, in response to determining that ingestible device 100 has reached a predetermined location within the GI tract. For example, ingestible device 100 may be configured to obtain a fluid sample from the GI tract in response to determining that the ingestible device has entered the jejunum portion of the small intestine (e.g., as determined by process 900 discussed in relation to FIG. 9). Other ingestible devices capable of obtaining samples or releasing substances are discussed in U.S. Ser. Nos. 14/460, 893, 15/680,400, and 15/699,848, the entire disclosure of each of which (as noted above) is incorporated by reference herein. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 100 may include a printed circuit board (PCB) 120, and a battery 128 configured to power PCB 120. PCB 120 may include a programmable microcontroller, and control and memory circuitry for holding and executing firmware or software for coordinating the operation of ingestible device 100, and the various components of ingestible device 100. For example, PCB 120 may include memory circuitry for storing data, such as data sets of measurements collected by sensing sub-unit 126, or instructions to be executed by control circuitry to implement a localization process, such as, for example, one or more of the processes, discussed herein, including those discussed below in connection with one or more of the associated flow charts. PCB 120 may include a detector 122 and an illuminator 124, which together form sensing sub-unit 126. In some embodiments, control circuitry within PCB 120 may include processing units, communication circuitry, or any other suitable type of circuitry for operating ingestible device 100. For illustrative purposes, only a single detector 122 and a single illuminator 124 forming a single sensing sub-unit 126 are shown. However, it is understood that in some embodiments there may be multiple sensing sub-units, each with a separate illuminator and detector, within ingestible device 100. For example, there may be several sensing sub-units spaced azimuthally around the circumference of the PCB 120, which may enable ingestible device 100 to transmit illumination and detect reflectances or ambient light in all directions around the circumference of the device. In some embodiments, sensing sub-unit 126 may be configured to generate an illumination using illuminator 124, which is directed through the window 114 in a radial direction away from ingestible device 100. This illumination may reflect off of the environment external to ingestible device 100, and the reflected light coming back into ingestible device 100 through window 114 may be detected as a reflectance by detector 122.

In some embodiments, window 114 may be of any suitable shape and size. For example, window 114 may extend around a full circumference of ingestible device 100. In some embodiments there may be a plurality of sensing sub-units (e.g., similar to sensing sub-unit 126) located at different positions behind the window. For example, three sensing sub-units may be positioned behind the window at the same longitudinal location, but spaced 120 degrees apart azimuthally. This may enable ingestible device 100 to transmit illuminations in all directions radially around ingestible device 100, and to measure each of the corresponding reflectances.

In some embodiments, illuminator 124 may be capable of producing illumination at a variety of different wavelengths in the ultraviolet, infrared, or visible spectrum. For example, illuminator 124 may be implemented by using Red-Green-Blue Light-Emitting diode packages (RGB-LED). These types of RGB-LED packages are able to transmit red, blue, or green illumination, or combinations of red, blue, or green illumination. Similarly, detector 122 may be configured to sense reflected light of the same wavelengths as the illumination produced by illuminator 124. For example, if illuminator 124 is configured to produce red, blue, or green illumination, detector 122 may be configured to detect different reflectances produced by red, blue, or green illumination (e.g., through the use of an appropriately configured photodiode). These detected reflectances may be stored by ingestible device 100 (e.g., within memory circuitry of PCB 120), and may then be used by ingestible device 100 in determining a location of ingestible device 100 within the GI tract (e.g., through the use of process 500 (FIG. 5), process 600 (FIG. 6), or process 900 (FIG. 9)).

It is understood that ingestible device 100 is intended to be illustrative, and not limiting. It will be understood that modifications to the general shape and structure of the various devices and mechanisms described in relation to FIG. 1 and FIG. 2 may be made without significantly changing the functions and operations of the devices and mechanisms. For example, ingestible device 100 may have a housing formed from a single piece of molded plastic, rather than being divided into a first end portion 104 and a second end portion 106. As an alternate example, the location of window 114 within ingestible device 100 may be moved to some other location, such as the center of ingestible device 100, or to one of the ends of ingestible device 100. Moreover, the systems and methods discussed in relation to FIGS. 1-10 may be implemented on any suitable type of ingestible device, provided that the ingestible device is capable of detecting reflectances or levels of illumination in some capacity. For example, in some embodiments ingestible device 100 may be modified to replace detector 122 with an image sensor, and the ingestible device may be configured to measure relative levels of red, blue, or green light by decomposing a recorded image into its individual spectral components. Other examples of ingestible devices with localization capabilities, which may be utilized in order to implement the systems and methods discussed in relation to FIG. 1-11, are discussed in U.S. Ser. No. 15/514,413, the entire contents of which (as noted above) are incorporated by reference herein. Furthermore, it should be noted that the features and limitations described in any one embodiment may be applied to any other embodiment herein, and the descriptions and examples relating to one embodiment may be combined with any other embodiment in a suitable manner.

Figure 3:
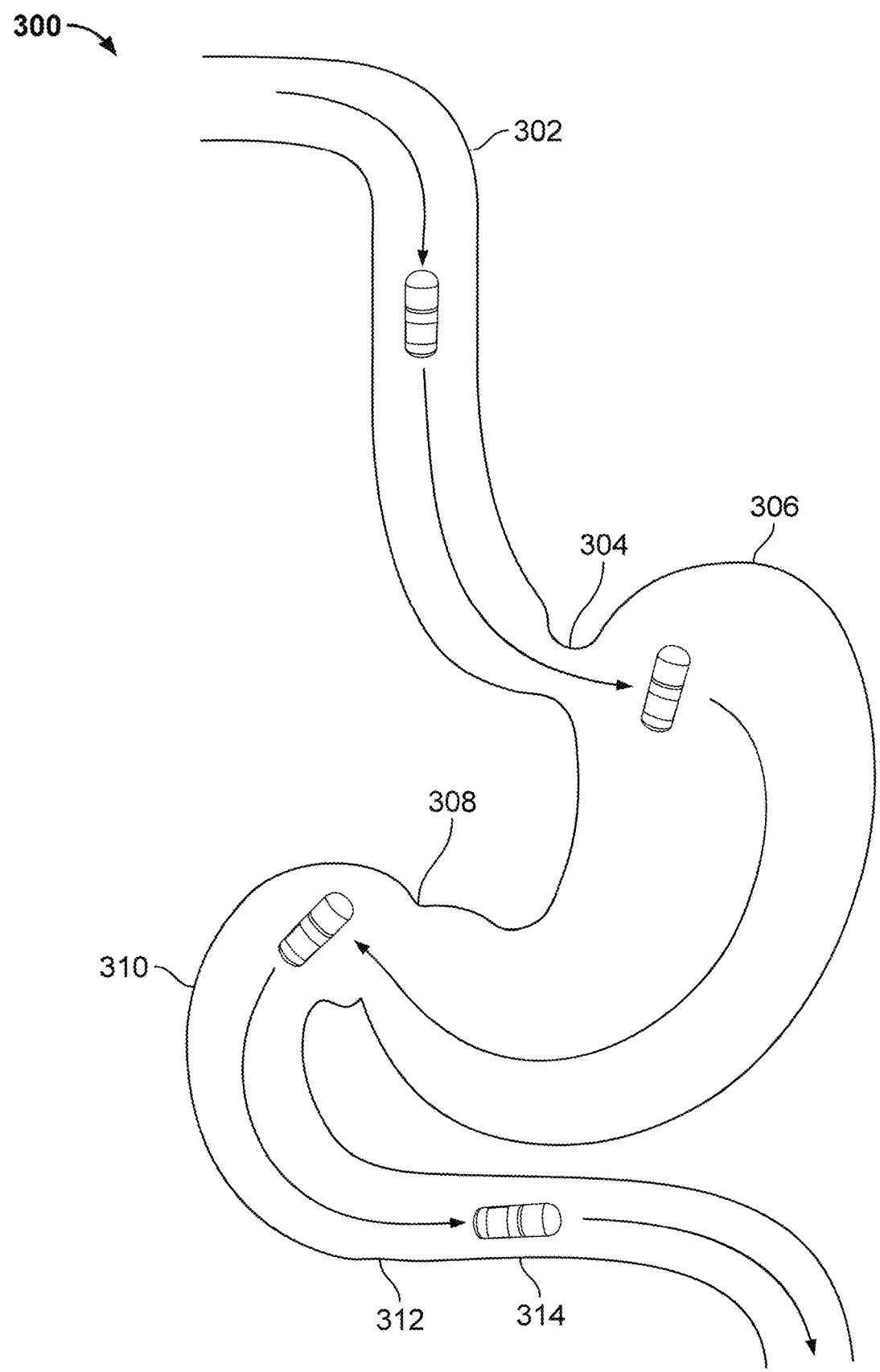
FIG. 3 is a diagram of an ingestible device during an example transit through a GI tract, in accordance with some embodiments of the disclosure.

FIG. 3 is a diagram of an ingestible device during an example transit through a gastrointestinal (GI) tract, in accordance with some embodiments of the disclosure. Ingestible device 300 may include any portion of any other ingestible device discussed in this disclosure (e.g., ingestible device 100 (FIG. 1)), and may be any suitable type of ingestible device with localization capabilities. For example, ingestible device 300 may be one embodiment of ingestible device 100 without the optional opening 116 (FIG. 1) or optional rotation assembly 118 (FIG. 2)). In some embodiments, ingestible device 300 may be ingested by a subject, and as ingestible device 300 traverses the GI tract, ingestible device 300 may be configured to determine its location within the GI tract. For example, the movement of ingestible device 300 and the amount of light detected by ingestible device 300 (e.g., via detector 122 (FIG. 2)) may vary substantially depending on the location of ingestible device 300 within the GI tract, and ingestible device 300 may be configured to use this information to determine a location of ingestible device 300 within the GI tract. For instance, ingestible device 300 may detect ambient light from the surrounding environment, or reflectances based on illumination generated by ingestible device 300 (e.g., generated by illuminator 124 (FIG. 1)), and use this information to determine a location of ingestible device 300 through (e.g., through the use of process 500 (FIG. 5), process 600 (FIG. 6), or process 900 (FIG. 9)). The current location of ingestible device 300, and the time that ingestible device 300 detected each transition between the various portions of the GI tract, may then be stored by ingestible device 300 (e.g., in memory circuitry of PCB 120 (FIG. 2)), and may be used for any suitable purpose.

Shortly after ingestible device 300 is ingested, ingestible device will traverse the esophagus 302, which may connect the subject's mouth to a stomach 306. In some embodiments, ingestible device 300 may be configured to determine that it has entered the esophagus portion GI tract by measuring the amount and type of light (e.g., via detector 122 (FIG. 2)) in the environment surrounding the ingestible device 300. For instance, ingestible device 300 may detect higher levels of light in the visible spectrum (e.g., via detector 122 (FIG. 2)) while outside the subject's body, as compared to the levels of light detected while within the GI tract. In some embodiments, ingestible device 300 may have previously stored data (e.g., on memory circuitry of PCB 120 (FIG. 2)) indicating a typical level of light detected when outside of the body, and the ingestible device 300 may be configured to determine that entry to the body has occurred when a detected level of light (e.g., detected via detector 122 (FIG. 2)) has been reduced beyond a threshold level (e.g., at least a 20-30% reduction) for a sufficient period of time (e.g., 5.0 seconds).

In some embodiments, ingestible device 300 may be configured to detect a transition from esophagus 302 to stomach 306 by passing through sphincter 304. In some embodiments, ingestible device 300 may be configured to determine whether it has entered stomach 306 based at least in part on a plurality of parameters, such as but not limited to the use of light or temperature measurements (e.g., via detector 122 (FIG. 2) or via a thermometer within ingestible device 300), pH measurements (e.g., via a pH meter within ingestible device 300), time measurements (e.g., as detected through the use of clock circuitry included within PCB 120 (FIG. 2)), or any other suitable information. For instance, ingestible device 300 may be configured to determine that ingestible device 300 has entered stomach 306 after detecting that a measured temperature of ingestible device 300 exceeds 31 degrees Celsius. Additionally or alternately, ingestible device 300 may be configured to automatically determine it has entered stomach 306 after one minute (or another pre-set time duration parameter, 80 seconds, 90 seconds, etc.) has elapsed from the time that ingestible device 300 was ingested, or one minute (or another pre-set time duration parameter, 80 seconds, 90 seconds, etc.) from the time that ingestible device 300 detected that it has entered the GI tract.

Stomach 306 is a relatively large, open, and cavernous organ, and therefore ingestible device 300 may have a relatively large range of motion. By comparison, the motion of ingestible device 300 is relatively restricted within the tube-like structure of the duodenum 310, the jejunum 314, and the ileum (not shown), all of which collectively form the small intestine. Additionally, the interior of stomach 306 has distinct optical properties from duodenum 310 and jejunum 314, which may enable ingestible device 300 to detect a transition from stomach 306 to duodenum 310 through the appropriate use of measured reflectances (e.g., through the use of reflectances measured by detector 122 (FIG. 2)), as used in conjunction with process 600 (FIG. 6)).

In some embodiments, ingestible device 300 may be configured to detect a pyloric transition from stomach 306 to duodenum 310 through the pylorus 308. For instance, in some embodiments, ingestible device 300 may be configured to periodically generate illumination in the green and blue wavelengths (e.g., via illuminator 124 (FIG. 2)), and measure the resulting reflectances (e.g., via detector 122 (FIG. 2)). Ingestible device 300 may be configured to then use a ratio of the detected green reflectance to the detected blue reflectance to determine whether ingestible device 300 is located within the stomach 306, or duodenum 310 (e.g., via process 600 (FIG. 6)). In turn, this may enable ingestible device 300 to detect a pyloric transition from stomach 306 to duodenum 310, an example of which is discussed in relation to FIG. 6.

Similarly, in some embodiments, ingestible device 300 may be configured to detect a reverse pyloric transition from duodenum 310 to stomach 306. Ingestible device 300 will typically transition naturally from stomach 306 to duodenum 310, and onward to jejunum 314 and the remainder of the GI tract. However, similar to other ingested substances, ingestible device 300 may occasionally transition from duodenum 310 back to stomach 306 as a result of motion of the subject, or due to the natural behavior of the organs with the GI tract. To accommodate this possibility, ingestible device 300 may be configured to continue to periodically generate illumination in the green and blue wavelengths (e.g., via illuminator 124 (FIG. 2)), and measure the resulting reflectances (e.g., via detector 122 (FIG. 2)) to detect whether or not ingestible device 300 has returned to stomach 306. An exemplary detection process is described in additional detail in relation to FIG. 6.

After entering duodenum 310, ingestible device 300 may be configured to detect a transition to the jejunum 314 through the duodenojejunal flexure 312. For example, ingestible device 300 may be configured to use reflectances to detect peristaltic waves within the jejunum 314, caused by the contraction of the smooth muscle tissue lining the walls of the jejunum 314. In particular, ingestible device 300 may be configured to begin periodically transmitting illumination (and measuring the resulting reflectances (e.g., via detector 122 and illuminator 124 of sensing sub-unit 126 (FIG. 2)) at a sufficiently high frequency in order to detect muscle contractions within the jejunum 314. Ingestible device 300 may then determine that it has entered the jejunum 314 in response to having detected either a first muscle contraction, or a predetermined number of muscle contractions (e.g., after having detected three muscle contractions in sequence). The interaction of ingestible device 300 with the walls of jejunum 314 is also discussed in relation to FIG. 4, and an example of this detection process is described in additional detail in relation to FIG. 9.

Figure 4:
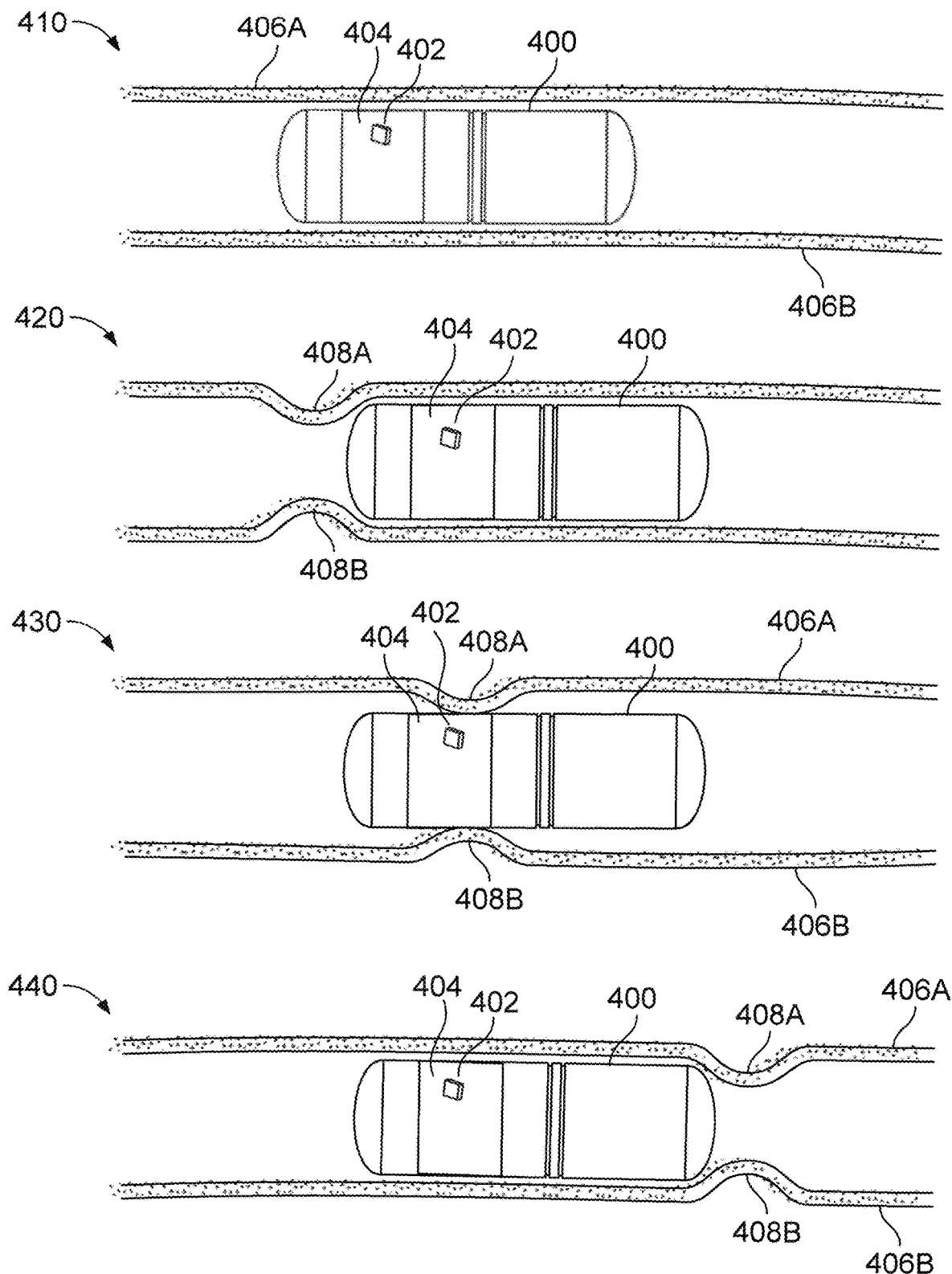
FIG. 4 is a diagram of an ingestible device during an example transit through a jejunum, in accordance with some embodiments of the disclosure.

FIG. 4 is a diagram of an ingestible device during an example transit through a jejunum, in accordance with some embodiments of the disclosure. Diagrams 410, 420, 430, and 440 depict ingestible device 400 as it traverses through a jejunum (e.g., jejunum 314), and how ingestible device 400 interacts with peristaltic waves formed by walls 406A and 406B (collectively, walls 406) of the jejunum. In some implementations, ingestible device 400 may include any portion of any other ingestible device discussed in this disclosure (e.g., ingestible device 100 (FIG. 1) or ingestible device 300 (FIG. 3)), and may be any suitable type of ingestible device with localization capabilities. For example, ingestible device 400 may be substantially similar to the ingestible device 300 (FIG. 3) or ingestible device 100 (FIG. 1), with window 404 being the same as window 114 (FIG. 1), and sensing sub-unit 402 being the same as sensing sub-unit 126 (FIG. 2).

Diagram 410 depicts ingestible device 400 within the jejunum, when the walls 406 of the jejunum are relaxed. In some embodiments, the confined tube-like structure of the jejunum naturally causes ingestible device 400 to be oriented longitudinally along the length of the jejunum, with window 404 facing walls 406. In this orientation, ingestible device 400 may use sensing sub-unit 402 to generate illumination (e.g., via illuminator 124 (FIG. 2)) oriented towards walls 406, and to detect the resulting reflectances (e.g., via detector 122 (FIG. 2)) from the portion of the illumination reflected off of walls 406 and back through window 404. In some embodiments, ingestible device 400 may be configured to use sensing sub-unit 402 to generate illumination and measure the resulting reflectance with sufficient frequency to detect peristaltic waves within the jejunum. For instance, in a healthy human subject, peristaltic waves may occur at a rate of approximately 0.05 Hz to 0.33 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds, which may improve the overall reliability of the detection process due to more data points being available. It is understood that the ingestible device 400 need not gather measurements at precise intervals, and in some embodiments the ingestible device 400 may be adapted to analyze data gathered at more irregular intervals, provided that there are still a sufficient number of appropriately spaced data points to detect 0.05 Hz to 0.33 Hz signals.

Diagram 420 depicts ingestible device 400 within the jejunum, when the walls 406 of the jejunum begin to contract and form a peristaltic wave. Diagram 420 depicts contracting portion 408A of wall 406A and contracting portion 408B of wall 406B (collectively, contracting portion 408 of wall 406) that form a peristaltic wave within the jejunum. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410).

Diagram 430 depicts ingestible device 400 within the jejunum, when the walls 406 of the jejunum continue to contract, squeezing around ingestible device 400. As the peristaltic wave proceeds along the length of the jejunum, contracting portions 408 of wall 406 may squeeze tightly around ingestible device 400, bringing the inner surface of wall 406 into contact with window 404. While in this position, ingestible device 400 may detect a change in a reflectance detected as a result of illumination produced by sensing sub-unit 402. The absolute value of the change in the measured reflectance may depend on several factors, such as the optical properties of the window 404, the spectral components of the illumination, and the optical properties of the walls 406. However, ingestible device 400 may be configured to store a data set with the reflectance values over time, and search for periodic changes in the data set consistent with the frequency of the peristaltic waves (e.g., by analyzing the data set in the frequency domain, and searching for peaks between 0.05 Hz to 0.33 Hz). This may enable ingestible device 400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 9, and an example of a reflectance data set gathered while ingestible device 400 is located within the jejunum is discussed in relation to FIG. 10.

Diagram 440 depicts ingestible device 400 within the jejunum, when the peristaltic wave has moved past ingestible device 400. Diagram 440 depicts contracting portions 408 that form the peristaltic wave within the jejunum having moved past the end of ingestible device 400. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410, or diagram 420).

Depending on the species of the subject, peristaltic waves may occur relatively with relatively predictable regularity. After the peristaltic wave has passed over ingestible device 400 (e.g., as depicted in diagram 440), the walls 406 of the jejunum may relax again (e.g., as depicted in diagram 410), until the next peristaltic wave begins to form. In some embodiments, ingestible device 400 may be configured to continue to gather reflectance value data while it is within the GI tract, and may store a data set with the reflectance values over time. This may allow ingestible device 400 to detect each of the muscle contractions as the peristaltic wave passes over ingestible device 400 (e.g., as depicted in diagram 430), and may enable ingestible device 400 to both count the number of muscle contractions that occur, and to determine that a current location of the ingestible device 400 is within the jejunum. For example, ingestible device 400 may be configured to monitor for possible muscle contractions while is inside either the stomach or the duodenum, and may determine that ingestible device 400 has moved to the jejunum in response to detecting a muscle contraction consistent with a peristaltic wave.

Figure 5:
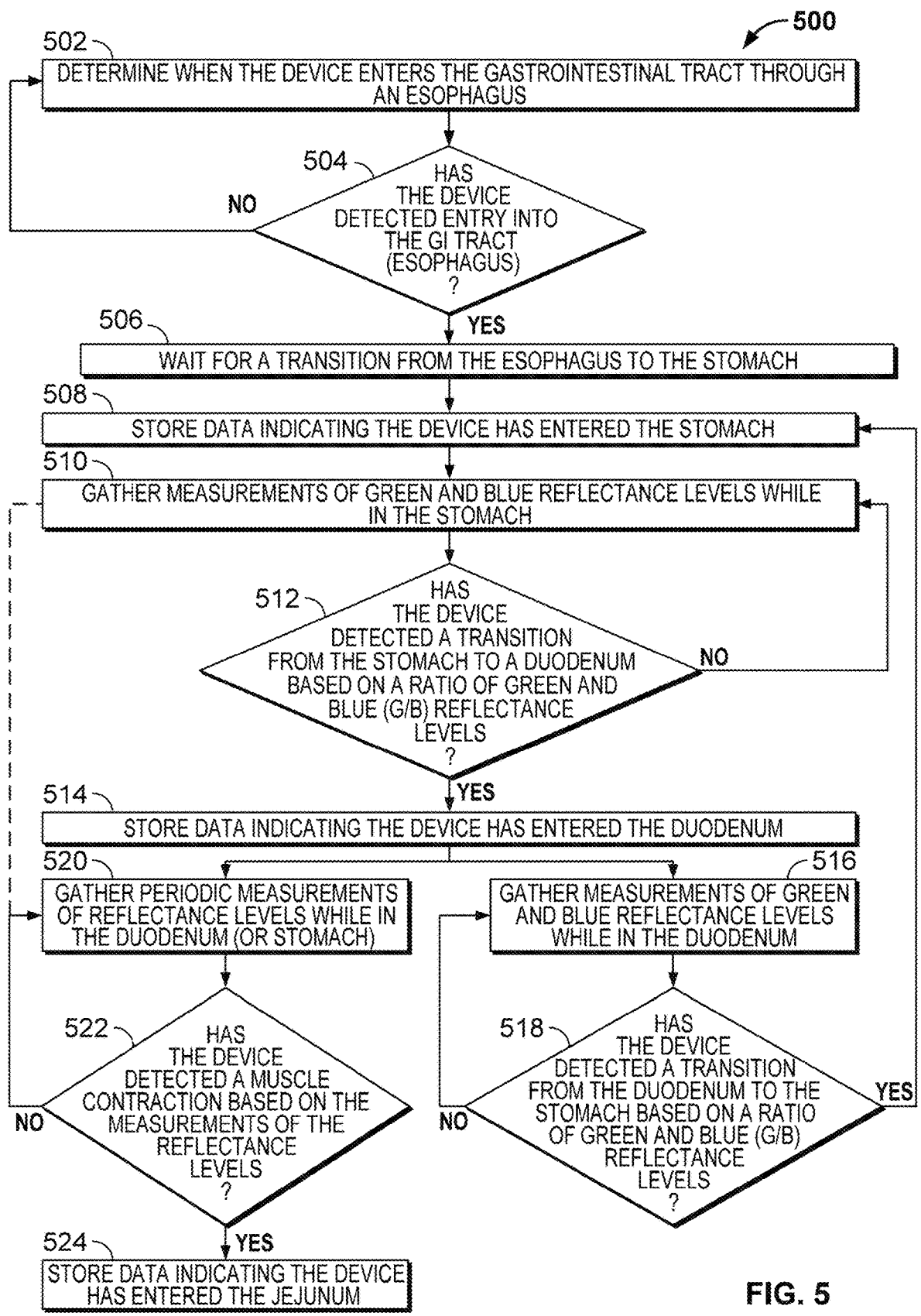
FIG. 5 is a flowchart of illustrative steps for determining a location of an ingestible device as it transits through a GI tract, in accordance with some embodiments of the disclosure.

FIG. 5 is a flowchart illustrating some aspects of a localization process used by the ingestible device. Although FIG. 5 may be described in connection with the ingestible device 100 for illustrative purposes, this is not intended to be limiting, and either portions or the entirety of the localization procedure 500 described in FIG. 5 may be applied to any device discussed in this application (e.g., the ingestible devices 100, 300, and 400), and any of the ingestible devices may be used to perform one or more parts of the process described in FIG. 5. Furthermore, the features of FIG. 5 may be combined with any other systems, methods or processes described in this application. For example, portions of the process in FIG. 5 may be integrated into or combined with the pyloric transition detection procedure described by FIG. 6, or the jejunum detection process described by FIG. 9.

At 502, the ingestible device (e.g., ingestible device 100, 300, or 400) gathers measurements (e.g., through detector 122 (FIG. 2)) of ambient light. For example, ingestible device 100 may be configured to periodically measure (e.g., through detector 122 (FIG. 2)) the level of ambient light in the environment surrounding ingestible device 100. In some embodiments, the type of ambient light being measured may depend on the configuration of detector 122 within ingestible device 100. For example, if detector 122 is configured to measure red, green, and blue wavelengths of light, ingestible device 100 may be configured to measure the ambient amount of red, green, and blue light from the surrounding environment. In some embodiments, the amount of ambient light measured by ingestible device 100 will be larger in the area external to the body (e.g., a well-lit room where ingestible device 100 is being administered to a subject) and in the oral cavity of the subject, as compared to the ambient level of light measured by ingestible device 100 when inside of an esophagus, stomach, or other portion of the GI tract (e.g., esophagus 302, stomach 306, duodenum 310, or jejunum 314 (FIG. 3)).

At 504, the ingestible device (e.g., ingestible device 100, 300, or 400) determines (e.g., via control circuitry within PCB 120 (FIG. 2)) whether the ingestible device has detected entry into the GI tract. For example, ingestible device 100 may be configured to determine when the most recent measurement of ambient light (e.g., the measurement gathered at 502) indicates that the ingestible device has entered the GI tract. For instance, the first time that ingestible device 100 gatherers a measurement of ambient light at 502, ingestible device 100 may store that measurement (e.g., via storage circuitry within PCB 120 (FIG. 2)) as a typical level of ambient light external to the body. Ingestible device 100 may be configured to then compare the most recent measurement of ambient light to the typical level of ambient light external to the body (e.g., via control circuitry within PCB 120 (FIG. 2)), and determine that ingestible device 100 has entered the GI tract when the most recent measurement of ambient light is substantially smaller than the typical level of ambient light external to the body. For example, ingestible device 100 may be configured to detect that it has entered the GI tract in response to determining that the most recent measurement of ambient light is less than or equal to 20% of the typical level of ambient light external to the body. If ingestible device 100 determines that it has detected entry into the GI tract (e.g., that ingestible device 100 has entered at least the esophagus 302 (FIG. 3)), process 500 proceeds to 506. Alternately, if ingestible device 100 determines that it has not detected entry into the GI tract (e.g., as a result of the most recent measurement being similar to the typical level of ambient light external to the body), process 500 proceeds back to 502 where the ingestible device 100 gathers further measurements. For instance, ingestible device 100 may be configured to wait a predetermined amount of time (e.g., five seconds, ten seconds, etc.), and then gather another measurement of the level of ambient light from the environment surrounding ingestible device 100.

At 506, the ingestible device (e.g., ingestible device 100, 300, or 400) waits for a transition from the esophagus to the stomach (e.g., from esophagus 302 to stomach 306 (FIG. 3)). For example, ingestible device 100 may be configured to determine that it has entered the stomach (e.g., stomach 306 (FIG. 3)) after waiting a predetermined period of time after having entered the GI tract. For instance, a typical esophageal transit time in a human patient may be on the order of 15-30 seconds. In this case, after having detected that ingestible device 100 has entered the GI tract at 504 (i.e., after detecting that ingestible device 100 has reached at least esophagus 302 (FIG. 3)), ingestible device 100 may be configured to wait one minute, or a similar amount of time longer than the typical esophageal transit time (e.g., ninety-seconds), before automatically determining that ingestible device 100 has entered at least the stomach (e.g., stomach 306 (FIG. 3)).

In some embodiments, the ingestible device (e.g., ingestible device 100, 300, or 400) may also determine it has entered the stomach based on measurements of pH or temperature. For example, ingestible device 100 may be configured to determine that it has entered the stomach if a temperature of ingestible device has increased to at least 31 degrees Celsius (i.e., consistent with the temperature inside the stomach), or if a measured pH of the environment surrounding ingestible device 100 is sufficiently acidic (i.e., consistent with the acidic nature of gastric juices that may be found inside the stomach).

At 508, the ingestible device (e.g., ingestible device 100, 300, or 400) stores data indicating the ingestible device has entered the stomach (e.g., stomach 306 (FIG. 3)). For example, after having waited a sufficient amount of time at 506, ingestible device 100 may store data (e.g., within storage circuitry of PCB 120 (FIG. 2)) indicative of ingestible device 100 having entered at least the stomach. Once ingestible device 100 reaches at least the stomach, process 500 proceeds to 510 where ingestible device 100 may be configured to gather data to detect entry into the duodenum (e.g., duodenum 310 (FIG. 3)).

In some embodiments, process 500 may also simultaneously proceed from 508 to 520, where ingestible device 100 may be configured to gather data in order to detect muscle contractions and detect entry into the jejunum (e.g., jejunum 314 (FIG. 3)). In some embodiments, ingestible device 100 may be configured to simultaneously monitor for entry into the duodenum at 516-518, as well as detect for entry into the jejunum at 520-524. This may allow ingestible device 100 to determine when it has entered the jejunum (e.g., as a result of detecting muscle contractions), even when it fails to first detect entry into the duodenum (e.g., as a result of very quick transit times of the ingestible device through the duodenum).

At 510, the ingestible device (e.g., ingestible device 100, 300, or 400) gathers measurements of green and blue reflectance levels (e.g., through the use of illuminator 124 and detector 122 of sensing sub-unit 126 (FIG. 2)) while in the stomach (e.g., stomach 306 (FIG. 3)). For example, ingestible device 100 may be configured to periodically gather measurements of green and blue reflectance levels while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within a stomach (e.g., stomach 306 (FIG. 3)), or a duodenum (e.g., duodenum 310 (FIG. 3)).

In some embodiments, the ingestible device (e.g., ingestible device 100, 300, or 400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 100 to sufficiently distinguish between the two wavelengths when detecting the reflectances (e.g., via detector 122 (FIG. 2)). It is understood that the separation of 50 nm is intended to be illustrative, and not limiting, and depending on the accuracy of the detectors within ingestible device 100, smaller separations may be possible to be used.

At 512, the ingestible device (e.g., ingestible device 100, 300, or 400) determines (e.g., using control circuitry within PCB 120 (FIG. 2)) whether the ingestible device has detected a transition from the stomach (e.g., stomach 306 (FIG. 3)) to a duodenum (e.g., duodenum 310 (FIG. 3)) based on a ratio of green and blue (G/B) reflectance levels. For example, ingestible device 100 may obtain (e.g., from memory circuitry of PCB 120 (FIG. 2)) a data set containing historical data for the respective ratio of the green reflectance to the blue reflectance as measured at a respective time. Generally speaking, a duodenum (e.g., duodenum 310 (FIG. 3)) of a human subject reflects a higher ratio of green light to blue light, as compared to the ratio of green light to blue light that is reflected by a stomach (e.g., stomach 306 (FIG. 3)). Based on this, ingestible device 100 may be configured to take a first set of ratios from the data set, representing the result of recent measurements, and compare them to a second set of ratios from the data set, representing the results of past measurements. When the ingestible device 100 determines that the mean value of the first set of ratios is substantially larger than the mean value of the second set of ratios (i.e., that the ratio of reflected green light to reflected blue light has increased), the ingestible device 100 may determine that it has entered the duodenum (e.g., duodenum 310 (FIG. 3)) from the stomach (e.g., stomach 306 (FIG. 3)). If the ingestible device 100 detects a transition from the stomach (e.g., stomach 306 (FIG. 3)) to a duodenum (e.g., duodenum 310 (FIG. 3)), process 500 proceeds to 514, where ingestible device 100 stores data indicating that the ingestible device 100 has entered the duodenum (e.g., duodenum 310 (FIG. 3)). Alternatively, if the ingestible device determines that the ingestible device has not transitioned from the stomach (e.g., stomach 306 (FIG. 3)) to the duodenum (e.g., duodenum 310 (FIG. 3)), process 500 proceeds back to 510 to gather more measurements of green and blue reflectance levels while still in the stomach (e.g., stomach 306 (FIG. 3)). An example procedure for using measurements of green and blue reflectances to monitor for transitions between the stomach and the duodenum is discussed in greater detail in relation to FIG. 6.

In some embodiments, the first time that ingestible device 100 detects a transition from the stomach (e.g., stomach 306 (FIG. 3)) to the duodenum (e.g., duodenum 310 (FIG. 3)), ingestible device 100 may be configured to take a mean of the second set of data, (e.g., the set of data previously recorded while in stomach 306 (FIG. 3)) and store this as a typical ratio of green light to blue light detected within the stomach (e.g., stomach 306 (FIG. 3)) (e.g., within memory circuitry of PCB 120 (FIG. 2)). This stored information may later be used by ingestible device 100 to determine when ingestible device 100 re-enters the stomach (e.g., stomach 306 (FIG. 3)) from the duodenum (e.g., duodenum 310 (FIG. 3)) as a result of a reverse pyloric transition.

At 514, the ingestible device (e.g., ingestible device 100, 300, or 400) stores data indicating that the ingestible device has entered the duodenum (e.g., duodenum 310 (FIG. 3)). For example, ingestible device 100 may store a flag within local memory (e.g., memory circuitry of PCB 120) indicating that the ingestible device 100 is currently in the duodenum. In some embodiments, the ingestible device 100 may also store a timestamp indicating the time when ingestible device 100 entered the duodenum. Once ingestible device 100 reaches the duodenum, process 500 proceeds to 520 where ingestible device 100 may be configured to gather data in order to detect muscle contractions and detect entry into the jejunum (e.g., jejunum 314 (FIG. 3)). Process 500 also proceeds from 514 to 516, where ingestible device 100 may be configured to gather data additional data in order to detect re-entry into the stomach (e.g., stomach 306 (FIG. 3)) from the duodenum (e.g., duodenum 310 (FIG. 3)).

At 516, the ingestible device (e.g., ingestible device 100, 300, or 400) gathers measurements (e.g., via sensing sub-unit 126 (FIG. 2)) of green and blue reflectance levels while in the duodenum (e.g., duodenum 310 (FIG. 3)). For example, ingestible device 100 may be configured to periodically gather measurements (e.g., via sensing sub-unit 126 (FIG. 2)) of green and blue reflectance levels while in the duodenum, similar to the measurements made at 510 while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within the duodenum (e.g., duodenum 310 (FIG. 3)), or if the ingestible device 100 has transitioned back into the stomach (e.g., stomach 306 (FIG. 3)).

At 518, the ingestible device (e.g., ingestible device 100, 300, or 400) determines a transition from the duodenum (e.g., duodenum 310 (FIG. 3)) to the stomach (e.g., stomach 306 (FIG. 3)) based on a ratio of the measured green reflectance levels to the measured blue reflectance levels. In some embodiments, ingestible device 100 may compare the ratio of the measured green reflectance levels to the measured blue reflectance levels recently gathered by ingestible device 100 (e.g., measurements gathered at 516), and determine whether or not the ratio of the measured green reflectance levels to the measured blue reflectance levels is similar to the average ratio of the measured green reflectance levels to the measured blue reflectance levels seen in the stomach (e.g., stomach 306 (FIG. 3)). For instance, ingestible device 100 may retrieve data (e.g., from memory circuitry of PCB 120 (FIG. 2)) indicative of the average ratio of the measured green reflectance levels to the measured blue reflectance levels seen in the stomach, and determine that ingestible device 100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 310 (FIG. 3)) to the stomach (e.g., stomach 306 (FIG. 3)), process 500 proceeds to 508 to store data indicating the ingestible device has entered the stomach (e.g., stomach 306 (FIG. 3)), and continues to monitor for further transitions. Alternatively, if the ingestible device does not detect a transition from the duodenum (e.g., duodenum 310 (FIG. 3)) to the stomach (e.g., stomach 306 (FIG. 3)), process 500 proceeds to 516 to gather additional measurements of green and blue reflectance levels while in the duodenum (e.g., duodenum 310 (FIG. 3)), which may be used to continuously monitor for possible transitions back into the stomach. An example procedure for using measurements of green and blue reflectances to monitor for transitions between the stomach and the duodenum is discussed in greater detail in relation to FIG. 6.

At 520, the ingestible device (e.g., ingestible device 100, 300, or 400) gathers periodic measurements of the reflectance levels (e.g., via sensing sub-unit 126 (FIG. 2)) while in the duodenum (e.g., duodenum 310 (FIG. 3)). In some embodiments, the ingestible device (e.g., ingestible device 100, 300, or 400) may gather similar periodic measurements while in the stomach as well. In some embodiments, these periodic measurements may enable ingestible device 100 to detect muscle contractions (e.g., muscle contractions due to a peristaltic wave as discussed in relation to FIG. 4), which may be indicative of entry into a jejunum (e.g., jejunum 314 (FIG. 3)). Ingestible device 100 may be configured to gather periodic measurements using any suitable wavelength of illumination (e.g., by generating illumination using illuminator 124, and detecting the resulting reflectance using detector 122 (FIG. 2)), or combinations of wavelengths of illumination. For example, in some embodiments, ingestible device 100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 100 at 520 may be sufficiently fast as to detect peristaltic waves in a subject. For instance, in a healthy human subject, peristaltic waves may occur at a rate of approximately 0.05 Hz to 0.33 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds or faster, and store values indicative of the resulting reflectances in a data set (e.g., within memory circuitry of PCB 120 (FIG. 2)). After gathering additional data (e.g., after gathering one new data point, or a predetermined number of new data points), process 500 proceeds to 522, where ingestible device 100 determines whether or not a muscle contraction has been detected.

At 522, the ingestible device (e.g., ingestible device 100, 300, or 400) determines (e.g., via control circuitry within PCB 120 (FIG. 0.2)) whether the ingestible device detects a muscle contraction based on the measurements of reflectance levels (e.g., as gathered by sensing sub-unit 126 (FIG. 2)). For example, ingestible device 100 may obtain a fixed amount of data stored as a result of measurements made at 520 (e.g., retrieve the past minute of data from memory circuitry within PCB 120 (FIG. 2)). Ingestible device 100 may then convert the obtained data into the frequency domain, and search for peaks in a frequency range that would be consistent with peristaltic waves. For example, in a healthy human subject, peristaltic waves may occur at a rate of approximately 0.05 Hz to 0.33 Hz, and an ingestible device 100 may be configured to search for peaks in the frequency domain representation of the data between 0.05 Hz and 0.33 Hz above a threshold value. If the ingestible device 100 detects a contraction based on the reflectance levels (e.g., based on detecting peaks in the frequency domain representation of the data between 0.05 Hz and 0.33 Hz), process 500 proceeds to 524 to store data indicating that the device has entered the jejunum. Alternatively, if the ingestible device 100 does not detect a muscle contraction, process 500 proceeds to 520 to gather periodic measurements of the reflectance levels while in the duodenum (e.g., duodenum 310 (FIG. 3)). In some embodiments, the ingestible device (e.g., ingestible device 100, 300, or 400) may store data (e.g., within memory circuitry of PCB 120 (FIG. 2)) indicating that a muscle contraction was detected, and process 500 will not proceed from 522 to 524 until a sufficient number of muscle contractions have been detected.

At 524, the ingestible device (e.g., ingestible device 100, 300, or 400) stores data (e.g., within memory circuitry of PCB 120 (FIG. 2)) indicating that the device has entered the jejunum (e.g., jejunum 314 (FIG. 3)). For example, in response to detecting that muscle contraction has occurred at 522, ingestible device 100 may determine that it has entered the jejunum 314, and is no longer inside of the duodenum (e.g., duodenum 310 (FIG. 3)) or the stomach (e.g., stomach 306 (FIG. 3)). In some embodiments, the ingestible device 100 may continue to measure muscle contractions while in the jejunum, and may store data indicative of the frequency, number, or strength of the muscle contractions over time (e.g., within memory circuitry of PCB 120 (FIG. 2)). In some embodiments, the ingestible device 100 may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device (e.g., ingestible device 100, 300, or 400) may also determine that it has entered the jejunum (e.g., jejunum 314 (FIG. 3)) after a predetermined amount of time has passed after having detected entry into the duodenum (e.g., duodenum 310 (FIG. 3)). For example, barring a reverse pyloric transition from the duodenum (e.g., duodenum 310 (FIG. 3)) back to the stomach (e.g., stomach 306 (FIG. 3)), the typical transit time for an ingestible device to reach the jejunum from the duodenum in a healthy human subject is less than three minutes. In some embodiments, the ingestible device (e.g., ingestible device 100, 300, or 400) may therefore be configured to automatically determine that it has entered the jejunum after spending at least three minutes within the duodenum. This determination may be made separately from the determination made based on measured muscle contractions (e.g., the determination made at 522), and in some embodiments, ingestible device 100 may determine that it has entered the jejunum in response to either detecting muscle contractions, or after three minutes has elapsed from having entered the duodenum (e.g., as determined by storing data at 514 indicative of the time that ingestible device entered the duodenum).

For illustrative purposes, 512-518 of process 500 describe the ingestible device (e.g., ingestible device 100, 300, or 400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 5, are merely illustrative. Any of the steps and descriptions of the flowcharts, including FIG. 5, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. As another example, ingestible device 100 may gather data periodic measurements and detect possible muscle contractions (e.g., at 520-522) while simultaneously gathering green and blue reflectance levels to determine transitions to and from the stomach and duodenum (e.g., at 510-518). Furthermore, it should be noted that the steps and descriptions of FIG. 5 may be combined with any other system, device, or method described in this application, including processes 600 (FIG. 6) and 900 (FIG. 9), and any of the ingestible devices or systems discussed in this application (e.g., ingestible devices 100, 300, or 400) could be used to perform one or more of the steps in FIG. 5.

Figure 6:
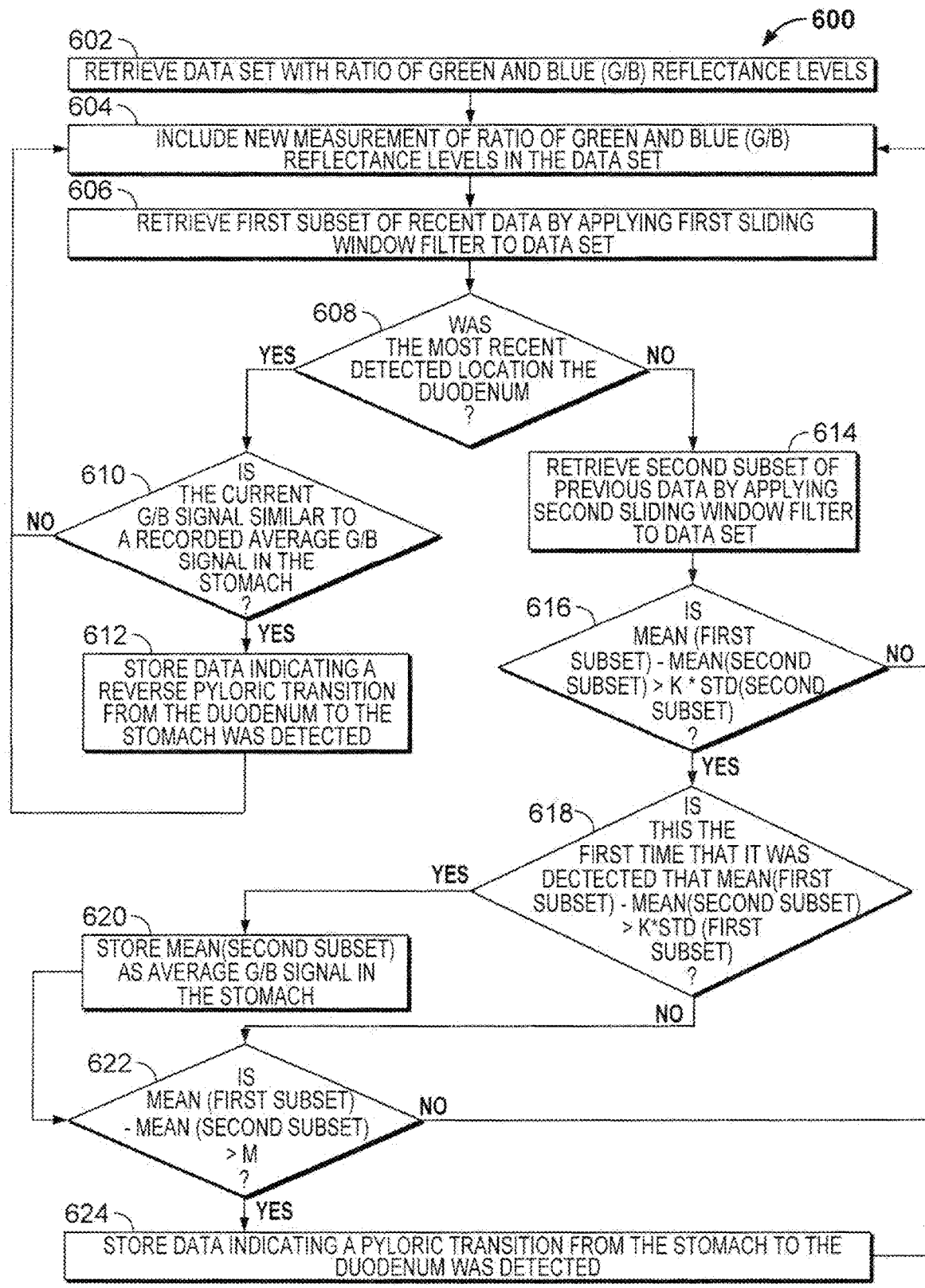
FIG. 6 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 6 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 600 may begin when an ingestible device first detects that it has entered the stomach, and will continue as long as the ingestible device determines that it is within the stomach or the duodenum. In some embodiments, process 600 may only be terminated when an ingestible device determines that it has entered the jejunum, or otherwise progressed past the duodenum and the stomach. Although FIG. 6 may be described in connection with the ingestible device 100 for illustrative purposes, this is not intended to be limiting, and either portions or the entirety of the duodenum detection process 600 described in FIG. 6 may be applied to any device discussed in this application (e.g., the ingestible devices 100, 300, or 400), and any of the ingestible devices may be used to perform one or more parts of the process described in FIG. 6. Furthermore, the features of FIG. 6 may be combined with any other systems, methods or processes described in this application. For example, portions of the process described by the process in FIG. 6 may be integrated into process 500 discussed in relation to FIG. 5.

At 602, the ingestible device (e.g., ingestible device 100, 300, or 400) retrieves a data set (e.g., from memory circuitry within PCB 120 (FIG. 2)) with ratios of the measured green reflectance levels to the measured blue reflectance levels over time. For example, ingestible device 100 may retrieve a data set from PCB 120 containing recently recorded ratios of the measured green reflectance levels to the measured blue reflectance levels (e.g., as recorded at 510 or 516 of process 500 (FIG. 5)). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 7 and FIG. 8.

At 604, the ingestible device (e.g., ingestible device 100, 300, or 400) includes a new measurement (e.g., as made with sensing sub-unit 126 (FIG. 2)) of a ratio of the measured green reflectance level to the measured blue reflectance level in the data set. For example, ingestible device 100 may be configured to occasionally record new data by transmitting green and blue illumination (e.g., via illuminator 124 (FIG. 2)), detecting the amount of reflectance received due to the green and blue illumination (e.g., via detector 122 (FIG. 2)), and storing data indicative of the amount of the received reflectance (e.g., in memory circuitry of PCB 120 (FIG. 2)). The ingestible device 100 may be configured to record new data every five to fifteen seconds, or at any other convenient interval of time. For illustrative purposes, ingestible device 100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of ingestible device 100 (e.g., stored as two separate data sets within memory circuitry of PCB 120 (FIG. 2)).

At 606, the ingestible device (e.g., ingestible device 100, 300, or 400) retrieves a first subset of recent data by applying a first sliding window filter to the data set. For example, ingestible device 100 may use a sliding window filter to obtain a predetermined amount of the most recent data within the data set, which may include any new values of the ratio of the measured green reflectance level to the measured blue reflectance level obtained at 604. For instance, the ingestible device may be configured to select between ten and forty data points from the data set, or ingestible device 100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 614).

In some embodiments, the ingestible device (e.g., ingestible device 100, 300, or 400) may also be configured to remove outliers from the data set, or to smooth out unwanted noise in the data set. For example, ingestible device 100 may select the first subset of data, or any other subset of data, by first obtaining a raw set of values by applying a window filter to the data set (e.g., selecting a particular range of data to be included). Ingestible device 100 may then be configured to identify outliers in the raw set of values; for instance, by identifying data points that are over three standard deviations away from the mean value of the raw set of values, or any other suitable threshold. Ingestible device 100 may then determine the subset of data by removing outliers from the raw set of values. This may enable ingestible device 100 to avoid spurious information when determining whether or not it is located within the stomach or the duodenum.

At 608, the ingestible device (e.g., ingestible device 100, 300, or 400) determines whether the most recently detected location was the duodenum (e.g., duodenum 310 (FIG. 3)). In some embodiments, ingestible device 100 may store a data flag (e.g., within memory circuitry of PCB 120 (FIG. 2)) indicating the most recent portion of the GI tract that the ingestible device 100 detected itself to be within. For instance, every time ingestible device 100 detects entry to the stomach (e.g., detects entry into stomach 306 (FIG. 3) as a result of the decision made at 610), a flag is stored in memory indicating the ingestible device 100 is in the stomach (e.g., as part of storing data at 612). If ingestible device 100 subsequently detects entry into the duodenum (e.g., detects entry into duodenum 310 (FIG. 3) as a result of a decision made at 624), another different flag is stored in memory indicating that the ingestible device 100 is in the duodenum (e.g., as part of storing data at 624). In this case, ingestible device 100 may retrieve the most recently stored flag at 608, and determine whether or not the flag indicates that the ingestible device 100 was most recently within the duodenum. If ingestible device 100 detects that it was most recently in the duodenum, process 600 proceeds to 610 where the ingestible device compares the recent measurements of the ratios of the measured green reflectance levels to the measured blue reflectance levels (e.g., measurements that include the recent measurement made at 606) to the typical ratios measured within the stomach, and uses this information to determine whether a reverse pyloric transition from the duodenum back to the stomach has occurred. Alternately, if ingestible device 100 detects that it was not most recently in the duodenum (e.g., because it was in the stomach instead), process 600 proceeds to 614 where the ingestible device compares the recent measurements of the ratios of the measured green reflectance levels to the measured blue reflectance levels (e.g., measurements that include the recent measurement made at 606) to past measurements, and uses this information to determine whether a pyloric transition from the stomach to the duodenum has occurred.

Process 600 proceeds from 608 to 610 when the ingestible device determined that it was most recently in the duodenum. At 610, the ingestible device (e.g., ingestible device 100, 300, or 400) determines (e.g., via control circuitry within PCB 120 (FIG. 2)) whether the current G/B signal is similar to a recorded average G/B signal in the stomach. For example, ingestible device 100 may be configured to have previously stored data (e.g., within memory circuitry of PCB 120 (FIG. 2)) indicative of the average ratio of the measured green reflectance levels to the measured blue reflectance levels measured in the stomach. Ingestible device 100 may then retrieve this stored data indicative of the average ratio of the measured green reflectance levels to the measured blue reflectance levels in the stomach, and compare this against the recent measurements in order to determine whether or not ingestible device 100 has returned back to the stomach from the duodenum. For instance, ingestible device 100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device 100 may determine whether or not the mean value of the first subset of data is less than "1.0+k*0.2," where "k" is a number between zero and five. It is understood that, in some embodiments, the ingestible device 100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 600 proceeds to 612 where ingestible device 100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 100 proceeds directly to 604, and continues to obtain new data on an ongoing basis.

At 612, the ingestible device (e.g., ingestible device 100, 300, or 400) stores data indicating a reverse pyloric transition from the duodenum to the stomach was detected. For example ingestible device 100 may store a data flag (e.g., within memory circuitry of PCB 120 (FIG. 2)) indicating that the ingestible device 100 most recently detected itself to be within the stomach portion of the GI tract (e.g., stomach 306 (FIG. 3)). In some embodiments, ingestible device 100 may also store data (e.g., within memory circuitry of PCB 120 (FIG. 2)) indicating a time that ingestible device 100 detected the reverse pyloric transition from the duodenum to the stomach. This information may be used by ingestible device 100 at 608, and as a result process 600 may proceed from 608 to 614, rather than proceeding from 618 to 610. After ingestible device 100 stores the data indicating a reverse pyloric transition from the duodenum to the stomach was detected, process 600 proceeds to 604 where ingestible device 100 continues to gather additional measurements, and continues to monitor for further transitions between the stomach and the duodenum.

Process 600 proceeds from 608 to 614 when the ingestible device determined that it was not most recently in the duodenum (e.g., as a result of having most recently been in the stomach instead). At 614, the ingestible device (e.g., ingestible device 100, 300, or 400) retrieves a second subset of previous data by applying a second sliding window filter to the data set. For example, ingestible device 100 may use a sliding window filter to obtain a predetermined amount of older data from a past time range, which may be separated from recent time range used to select the first subset of data gathered at 606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 100 recently transitioned to the stomach from the duodenum (e.g., as determined by checking for recent data stored within ingestible device 100 at 612), ingestible device 100 may select the second subset of data at 614 from a time frame when ingestible device 100 is known to be within the stomach. In some embodiments, ingestible device 100 may alternately select a previously recorded average and standard deviation for ratios of green reflectances and blue reflectances within the stomach (e.g., an average and standard deviation typical of data recorded within the stomach, as previously recorded within memory circuitry of PCB 120 at 620) in place of the second subset of data. In this case, ingestible device 100 may simply use the previously recorded average and previously recorded standard deviation when making a determination at 616, rather than expending resources to calculate the mean and standard deviation of the second subset.

At 616, the ingestible device (e.g., ingestible device 100, 300, or 400) determines whether the difference between the mean of the second subset and the mean of the first subset is greater than a predetermined multiple of the standard deviation of the first subset. For example, ingestible device 100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 600 proceeds to 618. Otherwise, process 600 proceeds back to 604, where the ingestible device 604 continues to gather new data to be used in monitoring for transitions between the stomach (e.g., stomach 306 (FIG. 3)) and the duodenum (e.g., duodenum 310 (FIG. 3)).

At 618, the ingestible device (e.g., ingestible device 100, 300, or 400) determines (e.g., via control circuitry within PCB 120 (FIG. 2)) whether the determination made at 616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 600 proceeds to 620 to store the mean of the second subset of past data as an average G/B signal in the stomach. Alternatively, if the ingestible device determines that the immediately preceding determination made at 616 is not the first time that the difference between the mean of the first subset of recent data and the mean of the second subset of past data is calculated to be greater than the standard deviation of the second subset, process 600 proceeds directly to 622.

At 620, the ingestible device (e.g., ingestible device 100, 300, or 400) stores the mean of the second subset as an average G/B signal in the stomach. For example, ingestible device 100 may be configured to store the mean of the second subset of past data (e.g., store within memory circuitry of PCB 120 (FIG. 2)) as the average ratio of the measured green reflectance levels to the measured blue reflectance levels measured in the stomach. In some embodiments, ingestible device 100 may also store the standard deviation of the second subset of past data as a typical standard deviation of the ratios of the measured green reflectance levels to the measured blue reflectance levels detected within the stomach. This stored information may be used by the ingestible device later on (e.g., at 610) to compare against future data, which may enable the ingestible device to detect reverse pyloric transitions from the duodenum (e.g., duodenum 310 (FIG. 3)) back to the stomach (e.g., stomach 306 (FIG. 3)), and may generally be used in place of other experimental data gathered from the stomach (e.g., in place of the second subset of data at 616). After storing the mean of the second subset as an average G/B signal in the stomach, process 600 proceeds to 622.

At 622, the ingestible device (e.g., ingestible device 100, 300, or 400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 0.1 to 0.5. If ingestible device 100 determines that the difference of the mean of the first subset of recent data to the second subset of past data is greater than a predetermined threshold, process 600 proceeds to 624 to store data indicating that a pyloric transition from the stomach to the duodenum (e.g., from stomach 306 to duodenum 310 (FIG. 3)) was detected. Alternatively, if the ingestible device determines that the ratio of the mean of the first subset to the second subset is less than or equal to the predetermined threshold, "M" (i.e., determines that a transition to the duodenum has not occurred), process 600 proceeds directly to 604 where ingestible device 100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 100, 300, or 400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 624, the ingestible device (e.g., ingestible device 100, 300, or 400) stores data indicating a pyloric transition from the stomach to the duodenum was detected. For example ingestible device 100 may store a data flag (e.g., within memory circuitry of PCB 120 (FIG. 2)) indicating that the ingestible device 100 most recently detected itself to be within the duodenum portion of the GI tract (e.g., duodenum 310 (FIG. 3)). In some embodiments, ingestible device 100 may also store data (e.g., within memory circuitry of PCB 120 (FIG. 2)) indicating a time that ingestible device 100 detected the pyloric transition from the stomach to the duodenum. This information may be used by ingestible device 100 at 608, and as a result process 600 may proceed from 608 to 610, rather than proceeding from 618 to 614. After ingestible device 100 stores the data indicating a pyloric transition from the stomach to the duodenum was detected, process 600 proceeds to 604 where ingestible device 100 continues to gather additional measurements, and continues to monitor for further transitions between the stomach and the duodenum.

It will be understood that the steps and descriptions of the flowcharts of this disclosure, including FIG. 6, are merely illustrative. Any of the steps and descriptions of the flowcharts, including FIG. 6, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. Furthermore, it should be noted that the steps and descriptions of FIG. 6 may be combined with any other system, device, or method described in this application, and any of the ingestible devices or systems discussed in this application could be used to perform one or more of the steps in FIG. 6. For example, portions of process 600 may be incorporated into 508-516 of process 500 (FIG. 5), and may be part of a more general process for determining a location of the ingestible device. As another example, the ratio of detected blue and green light (e.g., as measured and added to the data set at 604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 7 and FIG. 8 below.

Figure 7:
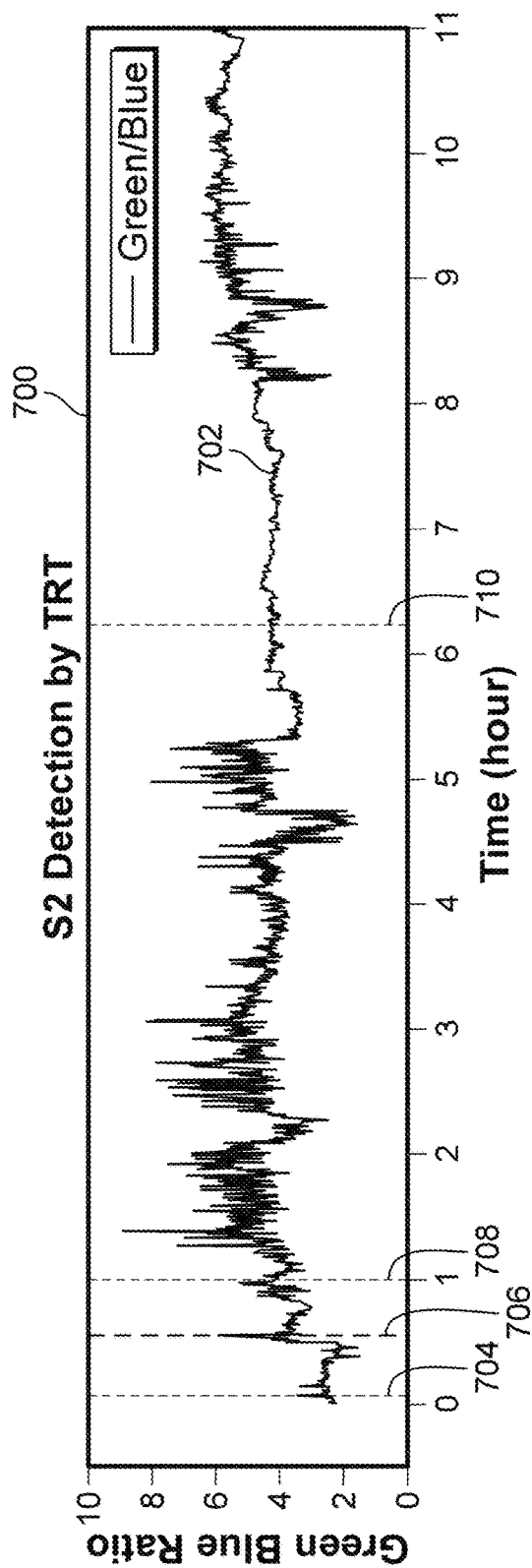
FIG. 7 is a plot illustrating data collected during an example operation of an ingestible device, which may be used when determining a location of an ingestible device as it transits through a GI tract, in accordance with some embodiments of the disclosure.

FIG. 7 is a plot illustrating data collected during an example operation of an ingestible device (e.g., ingestible device 100, 300, or 400), which may be used when determining a location of an ingestible device as it transits through a gastrointestinal (GI) tract, in accordance with some embodiments of the disclosure.

Although FIG. 7 may be described in connection with ingestible device 100 for illustrative purposes, this is not intended to be limiting, and plot 700 and data set 702 may be typical of data gathered by any device discussed in this application. Plot 700 depicts the ratios of the measured green reflectance levels to the measured blue reflectance levels over time. For example, ingestible device 100 may have computed the value for each point in the data set 702 by transmitting green and blue illumination at a given time (e.g., via illuminator 124 (FIG. 2)), measuring the resulting green and blue reflectances (e.g., via detector 122 (FIG. 2)), calculating the ratio of the resulting reflectances, and storing the ratio in the data set along with a timestamp indicating the time that the reflectances were gathered.

At 704, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels, and at 706 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 702 around 706 jump up precipitously, which is indicative of the higher ratios of measured green reflectance levels to measured blue reflectance levels typical of the duodenum.

The remainder of the data set 702 depicts the ratios of the measured green reflectance levels to the measured blue reflectance levels throughout the remainder of the GI tract. At 708, ingestible device 100 has reached the jejunum (e.g., as determined through measurements of muscle contractions, as discussed in relation to FIG. 9), and by 710, ingestible device 100 has reached the cecum. It is understood that, in some embodiments, the overall character and appearance of data set 702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 100 may measure a relatively stable ratio of the measured green reflectance levels to the measured blue reflectance levels. In some embodiments, ingestible device 100 may be configured to determine transitions from the small intestine to the cecum based on these differences. For example, ingestible device 100 may compare recent windows of data to past windows of data, and detect a transition to the cecum in response to determining that the standard deviation of the ratios in the recent window of data is substantially less than the standard deviation of the ratios in the past window of data.

Figure 8:
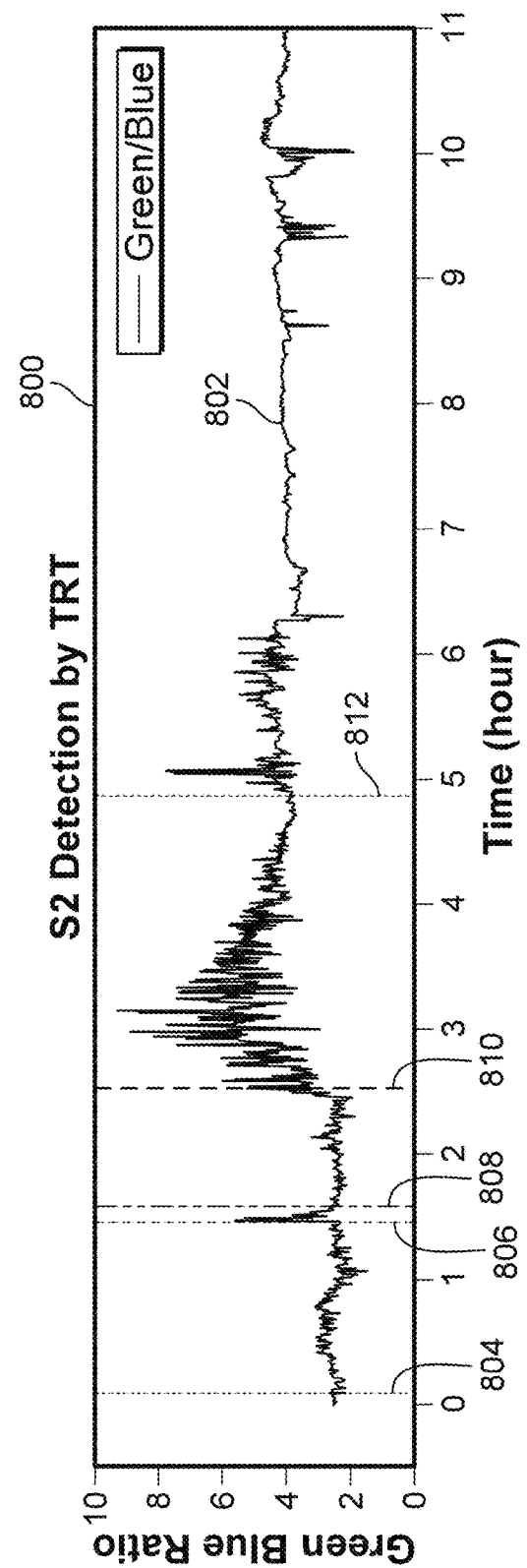
FIG. 8 is another plot illustrating data collected during an example operation of an ingestible device, which may be used when determining a location of an ingestible device as it transits through a GI tract, in accordance with some embodiments of the disclosure.

FIG. 8 is another plot illustrating data collected during an example operation of an ingestible device, which may be used when determining a location of an ingestible device as it transits through a gastrointestinal (GI) tract, in accordance with some embodiments of the disclosure. Similar to FIG. 7, FIG. 8 may be described in connection with the ingestible device 100 for illustrative purposes. However, this is not intended to be limiting, and plot 800 and data set 802 may be typical of data gathered by any device discussed in this application.

At 804, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels (e.g., via sensing sub-unit 126 (FIG. 2)), and at 806 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 802 around 806 jump up precipitously, which is indicative of the higher ratios of measured green reflectance levels to measured blue reflectance levels typical of the duodenum, before falling shortly thereafter. As a result of the reduced values in data set 802, ingestible device 100 determines that a reverse pyloric transition has occurred from the duodenum back to the stomach at 808 (e.g., as a result of making a determination similar to the determinations discussed in relation to 610-612 of process 600 (FIG. 6)). At 810, as a result of the values in data set 802 increasing again, ingestible device 100 determines that another pyloric transition has occurred from the stomach to the duodenum, and shortly thereafter ingestible device 100 proceeds onwards to the jejunum, ileum, and cecum.

The remainder of the data set 802 depicts the ratios of the measured green reflectance levels to the measured blue reflectance levels throughout the remainder of the GI tract. Notably, at 812, ingestible device reaches the transition point between the ileum and the cecum. As discussed above in relation to FIG. 7, the transition to the cecum is marked by a reduced standard deviation in the ratios of measured green reflectances and measured blue reflectances over time, and ingestible device 100 may be configured to detect a transition to the cecum based on determining that the standard deviation of a recent set of measurements is substantially smaller than the standard deviation of past measurements taken from the jejunum or ileum.

Figure 9:
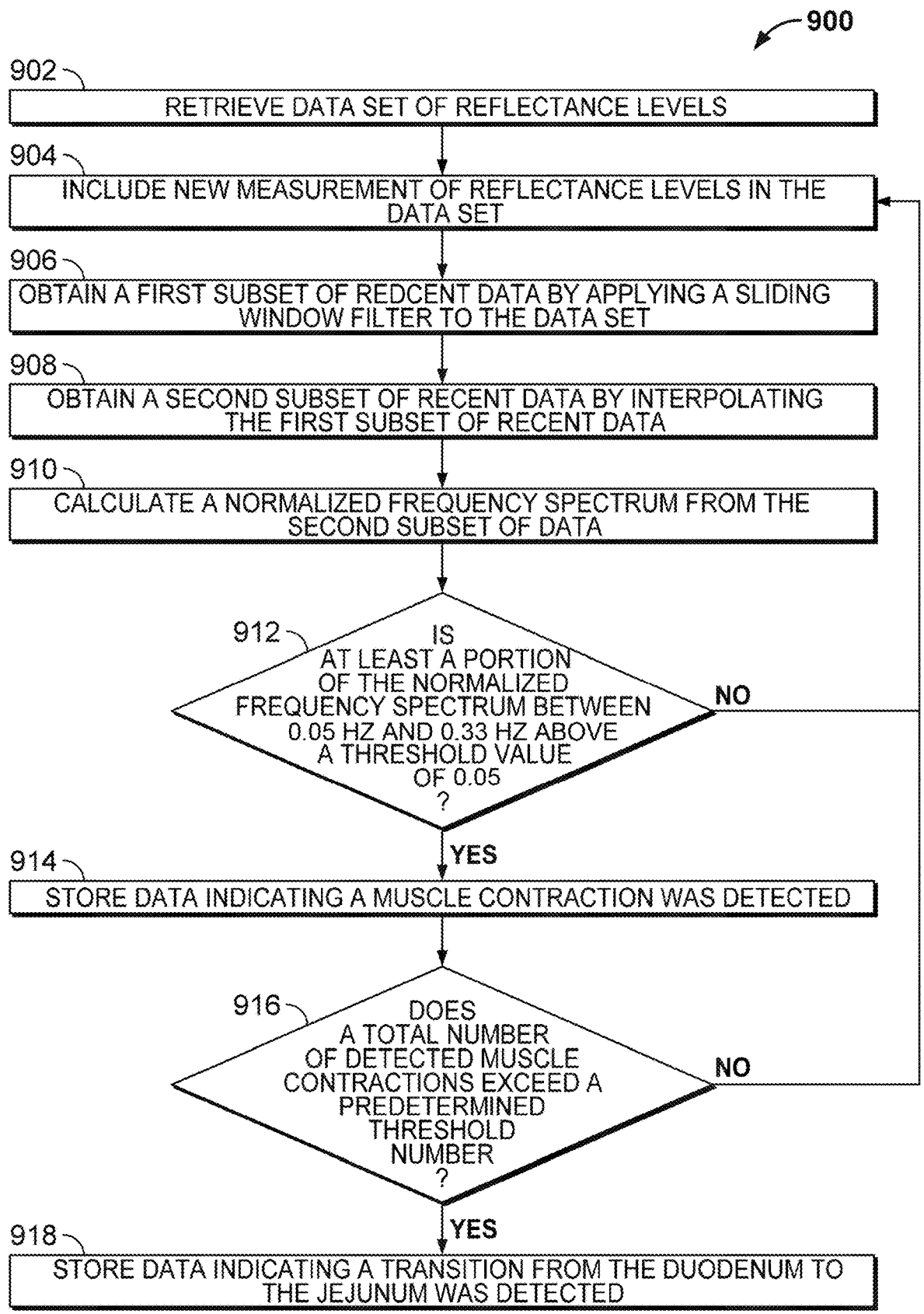
FIG. 9 is a flowchart of illustrative steps for detecting a transition from a duodenum to a jejunum, which may be used when determining a location of an ingestible device as it transits through a GI tract, in accordance with some embodiments of the disclosure.

FIG. 9 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 9 may be described in connection with the ingestible device 100 for illustrative purposes, this is not intended to be limiting, and either portions or the entirety of process 900 described in FIG. 9 may be applied to any device discussed in this application (e.g., the ingestible devices 100, 300, and 400), and any of these ingestible devices may be used to perform one or more parts of the process described in FIG. 9. Furthermore, the features of FIG. 9 may be combined with any other systems, methods or processes described in this application. For example, portions of the process described by the process in FIG. 9 may be integrated into the localization process described by FIG. 5 (e.g., as part of 520-524 of process 500 (FIG. 5)). In some embodiments, an ingestible device 100 may perform process 900 while in the duodenum, or in response to detecting entry to the duodenum. In other embodiments, an ingestible device 100 may perform process 900 while in the stomach, or in response to detecting entry into the GI tract. It is also understood that process 900 may be performed in parallel with any other process described in this disclosure (e.g., process 600 (FIG. 6)), which may enable ingestible device 100 to detect entry into various portions of the GI tract, without necessarily detecting entry into a preceding portion of the GI tract.

For illustrative purposes, FIG. 9 may be discussed in terms of ingestible device 100 generating and making determinations based on a single set of reflectance levels generated at a single wavelength by a single sensing sub-unit (e.g., sensing sub-unit 126 (FIG. 2)). However, it is understood that ingestible device 100 may generate multiple wavelengths of illumination from multiple different sensing sub-units positioned around the circumference of ingestible device (e.g., multiple sensing sub-units positioned at different locations behind window 114 of ingestible device 100 (FIG. 1), and each of the resulting reflectances may be stored as a separate data set. Moreover, each of these sets of reflectance levels may be used to detect muscle contractions by running multiple versions of process 900, each one of which processes data for a different set of reflectances corresponding to data sets obtained from measurements of different wavelengths or measurements made by different sensing sub-units.

At 902, the ingestible device (e.g., ingestible device 100, 300, or 400) retrieves a set of reflectance levels. For example, ingestible device 100 may retrieve a data set of previously recorded reflectance levels from memory (e.g., from memory circuitry of PCB 120 (FIG. 2)). Each of the reflectance levels may correspond to reflectances previously detected by ingestible device 100 (e.g., via detector 122 (FIG. 2)) from illumination generated by ingestible device 100 (e.g., via illuminator 124 (FIG. 2)), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 100 at periodic intervals.

At 904, the ingestible device (e.g., ingestible device 100, 300, or 400) includes new measurements of reflectance levels in the data set. For example, ingestible device 100 may be configured to detect a new reflectance (e.g., transmit illumination and detect the resulting reflectance using sensing sub-unit 126 (FIG. 2)) at regular intervals, or with sufficient speed as to detect peristaltic waves. For example, ingestible device 100 may be configured to generate illumination and measure the resulting reflectance once every three seconds (i.e., the minimum rate necessary to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 100 makes a new reflectance level measurement at 904, the new data is included to the data set (e.g., a data set stored within memory circuitry of PCB 120 (FIG. 2)).

At 906, the ingestible device (e.g., ingestible device 100, 300, or 400) obtains a first subset of recent data by applying a sliding window filter to the data set. For example, ingestible device 100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.05 Hz to 0.33 Hz for healthy human subjects). In some embodiments, ingestible device 100 may also clean the data, for example, by removing outliers from the first subset of data obtained through the use of the sliding window filter.

At 908, the ingestible device (e.g., ingestible device 100, 300, or 400) obtains a second subset of recent data by interpolating the first subset of recent data. For example, ingestible device 100 may interpolate the first subset of data in order to generate a second subset of data with a sufficient number of data points (e.g., data points spaced every 0.5 seconds or greater). In some embodiments, this may enable ingestible device 100 to also replace any outlier data points that may have been removed as part of applying the window filter at 906.

At 910, the ingestible device (e.g., ingestible device 100, 300, or 400) calculates a normalized frequency spectrum from the second subset of data. For example, ingestible device 100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 100 may be configured to have pre-stored values of a normalized discreet Fourier transform (DFT) matrix, or the rows of the DFT matrix corresponding to the 0.05 Hz to 0.33 Hz frequency components of interest, within memory (e.g., memory circuitry of PCB 120 (FIG. 2)). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 10.

At 912, the ingestible device (e.g., ingestible device 100, 300, or 400) determines whether at least a portion of the normalized frequency spectrum is between 0.05 Hz and 0.33 Hz above a threshold value of 0.5 Hz. Peristaltic waves in a healthy human subject occur at a rate between 0.05 Hz and 0.33 Hz, and an ingestible device experiencing peristaltic waves (e.g., ingestible device 400 detecting contractions in walls 406 of the jejunum (FIG. 4)) may detect sinusoidal variations in the amplitude of detected reflectances levels that follow a similar 0.05 Hz to 0.33 Hz frequency. If the ingestible device determines that a portion of the normalized frequency spectrum between 0.05 Hz and 0.33 Hz is above a threshold value of 0.5, this measurement may be consistent with peristaltic waves in a healthy human subject, and process 900 proceeds to 914 where ingestible device 100 stores data indicating a muscle contraction was detected. Alternatively, if the ingestible device determines that no portion of the normalized frequency spectrum between 0.05 Hz and 0.33 Hz above a threshold value of 0.5, process 900 proceeds directly to 904 to make new measurements and to continue to monitor for new muscle contractions. It is understood that a threshold value other than 0.5 may be used, and that the exact threshold may depend on the sampling frequency and type of frequency spectrum used by ingestible device 100.

At 914, the ingestible device (e.g., ingestible device 100, 300, or 400) stores data indicating a muscle contraction was detected. For example, ingestible device 100 may store data in memory (e.g., memory circuitry of PCB 120 (FIG. 2)) indicating that a muscle contraction was detected, and indicating the time that the muscle contraction was detected. In some embodiments, ingestible device 100 may also monitor the total number of muscle contractions detected, or the number of muscle contractions detected in a given time frame. In some embodiments, detecting a particular number of muscle contractions may be consistent with ingestible device 100 being within the jejunum (e.g., jejunum 314 (FIG. 3)) of a healthy human subject. After detecting a muscle contraction, process 900 proceeds to 916.

At 916, the ingestible device (e.g., ingestible device 100, 300, or 400) determines whether a total number of muscle contractions exceeds a predetermined threshold number. For example, ingestible device 100 may retrieve the total number of muscle contractions detected from memory (e.g., from memory circuitry of PCB 120 (FIG. 2)), and compare the total number to a threshold value. In some embodiments, the threshold value may be one, or any number larger than one. The larger the threshold value, the more muscle contractions need to be detected before ingestible device 100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 900 proceeds to 918 to store data indicating detection of a transition from the duodenum to the jejunum. Alternatively, if the total number of contractions does not exceed a predetermined threshold number, process 900 proceeds to 904 to include new measurements of reflectance levels in the data set. An example plot of the muscle contractions detected over time is discussed in greater detail in relation to FIG. 11.

At 918, the ingestible device (e.g., ingestible device 100, 300, or 400) stores data indicating detection of a transition from the duodenum to the jejunum. For example, ingestible device 100 may store data in memory (e.g., from memory circuitry of PCB 120 (FIG. 2)) indicating that the jejunum has been reached. In some embodiments, if ingestible device 100 is configured to perform all or part of process 900 while in the stomach, ingestible device 100 may store data at 918 indicating detection of a transition from the stomach directly to the jejunum (e.g., as a result of transitioning too quickly through the duodenum for the pyloric transition to be detected using process 600 (FIG. 6)).

In some embodiments, the ingestible device (e.g., ingestible device 100, 300, or 400) may be configured to obtain a fluid sample from the environment external to a housing of the ingestible device in response to identifying a change in the location of the ingestible device. For example, ingestible device 100 may be configured to obtain a fluid sample from the environment external to the housing of ingestible device 100 (e.g., through the use of optional opening 116 and optional rotating assembly 118 (FIG. 2)) in response to determining that the ingestible device is located within the jejunum (e.g., jejunum 314 (FIG. 3)). In some embodiments, ingestible device 100 may also be equipped with appropriate diagnostics to detect certain medical conditions based on the retrieved fluid sample, such as small intestinal bacterial overgrowth (SIBO).

In some embodiments, the ingestible device (e.g., ingestible device 100, 300, or 400) may be configured to deliver a dispensable substance that is pre-stored within the ingestible device from the ingestible device into the gastrointestinal tract in response to identifying the change in the location of the ingestible device. For example, ingestible device 100 may have a dispensable substance pre-stored within the ingestible device 100 (e.g., within a storage chamber or cavity on optional storage sub-unit 118-3 (FIG. 2)), and ingestible device 100 may be configured to dispense the substance into the gastrointestinal tract (e.g., through the use of optional opening 116 and optional rotating assembly 118 (FIG. 2)) when the ingestible device 100 detects that the ingestible device 100 is located within the jejunum (e.g., jejunum 314 (FIG. 3)). In some embodiments, this may enable ingestible device 100 to deliver substances (e.g., therapeutics and medicaments) at targeted locations within the GI tract.

In some embodiments, the ingestible device (e.g., ingestible device 100, 300, or 400) may be configured to perform an action based on the total number of detected muscle contractions. For example, ingestible device 100 may be configured to retrieve data indicative of the total number of muscle contractions (e.g., from memory circuitry of PCB 120 (FIG. 2)), and compare that to an expected number muscle contractions in a healthy individual. In response, the ingestible device may either dispense a substance into the gastrointestinal tract (e.g., through the use of optional opening 116 and optional rotating assembly 118 (FIG. 2)), or may obtain a fluid sample from the environment external to the housing of ingestible device 100 (e.g., through the use of optional opening 116 and optional rotating assembly 118 (FIG. 2)). For instance, ingestible device 100 may be configured to obtain a sample in response to determining that a number of detected muscle contractions is abnormal, and differs greatly from the expected number. As another example, ingestible device 100 may be configured to deliver a substance into the GI tract (such as a medicament), in response to determining that the detected muscle contractions are consistent with a functioning GI tract in a healthy individual.

It will be understood that the steps and descriptions of the flowcharts of this disclosure, including FIG. 9, are merely illustrative. Any of the steps and descriptions of the flowcharts, including FIG. 9, may be modified, omitted, rearranged, performed in alternate orders or in parallel, two or more of the steps may be combined, or any additional steps may be added, without departing from the scope of the present disclosure. For example, the ingestible device 100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 9 may be combined with any other system, device, or method described in this application, and any of the ingestible devices or systems discussed in this application could be used to perform one or more of the steps in FIG. 9.

Figure 10:
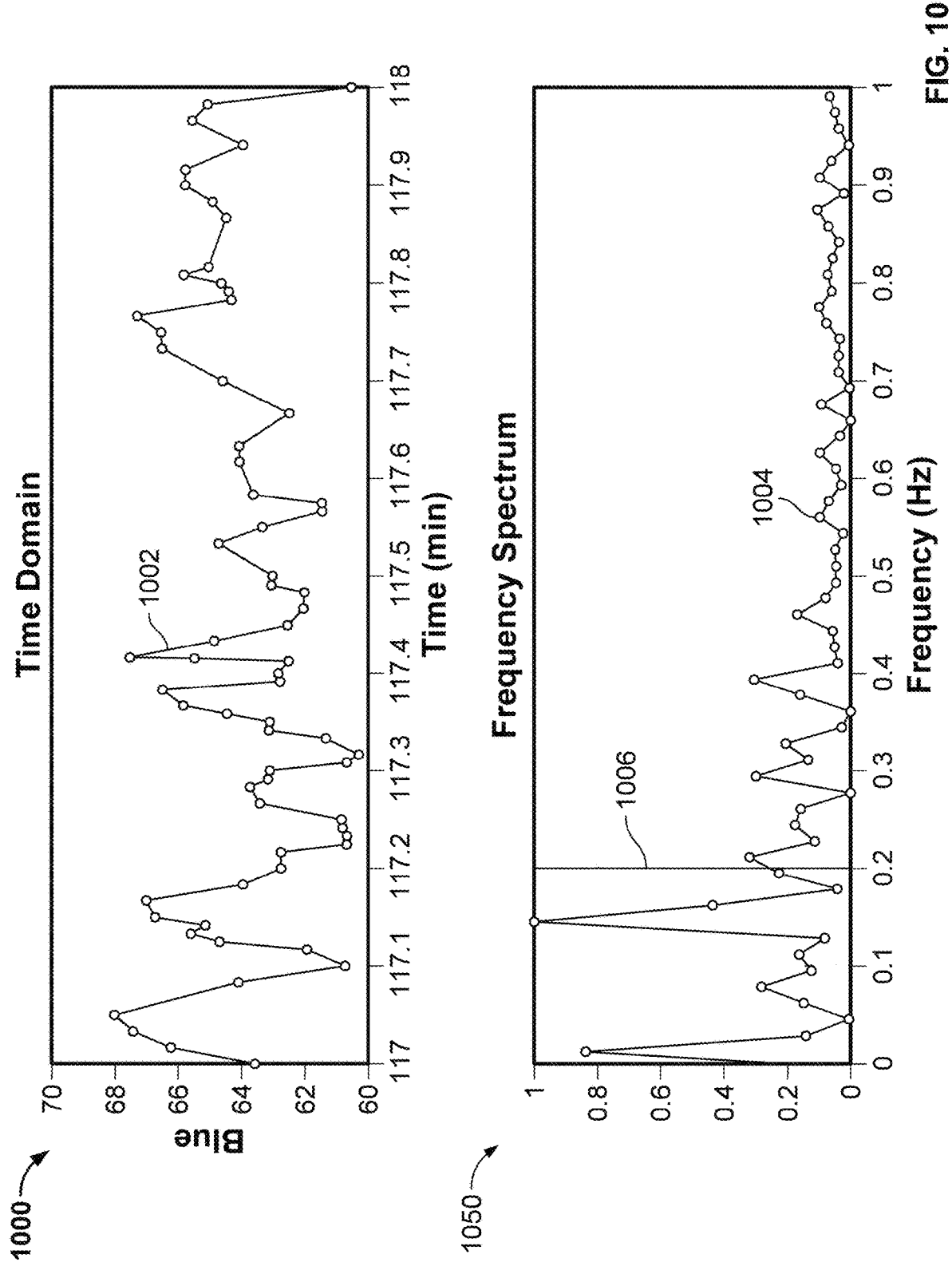
FIG. 10 is a plot illustrating data collected during an example operation of an ingestible device, which may be used when detecting a transition from a duodenum to a jejunum, in accordance with some embodiments of the disclosure.

FIG. 10 is a plot illustrating data collected during an example operation of an ingestible device, which may be used when detecting a transition from a duodenum to a jejunum, in accordance with some embodiments of the disclosure. Diagram 1000 depicts a time domain plot 1002 of a data set of reflectance levels measured by an ingestible device (e.g., the second subset of data discussed in relation to 908 of FIG. 9). In some embodiments, ingestible device 100 may be configured to gather data points at semi-regular intervals approximately 0.5 seconds apart. By comparison, diagram 1050 depicts a frequency domain plot 1004 of the same data set of reflectance levels measured by an ingestible device (e.g., as a result of ingestible device 100 calculating a frequency spectrum at 910 of FIG. 9). In some embodiments, ingestible device 100 may be configured to calculate the frequency spectrum through any convenient means.

In diagram 1050, the range of frequencies 1006 between 0.05 Hz and 0.33 Hz may be the range of frequencies that ingestible device 100 searches in order to detect muscle contractions. As shown in diagram 1050, there is a strong peak in the frequency domain plot 1004 around 0.14 Hz, which is consistent with the frequency of peristaltic motion in a healthy human individual. In this case, an ingestible device 100 analyzing frequency domain plot 1004 may be configured to determine that the data is consistent with a detected muscle contraction (e.g., using a process similar to 912 of process 900 (FIG. 9)), and may store data (e.g., in memory circuitry of PCB 120 (FIG. 2)) indicating that a muscle contraction has been detected. Because the muscle contraction was detected from the one-minute window of data ending at 118 minutes, ingestible device 100 may also store data indicating that the muscle contraction was detected at the 118-minute mark (i.e., which may indicate that the ingestible device 100 was turned on and ingested by the subject 118 minutes ago).

Figure 11:
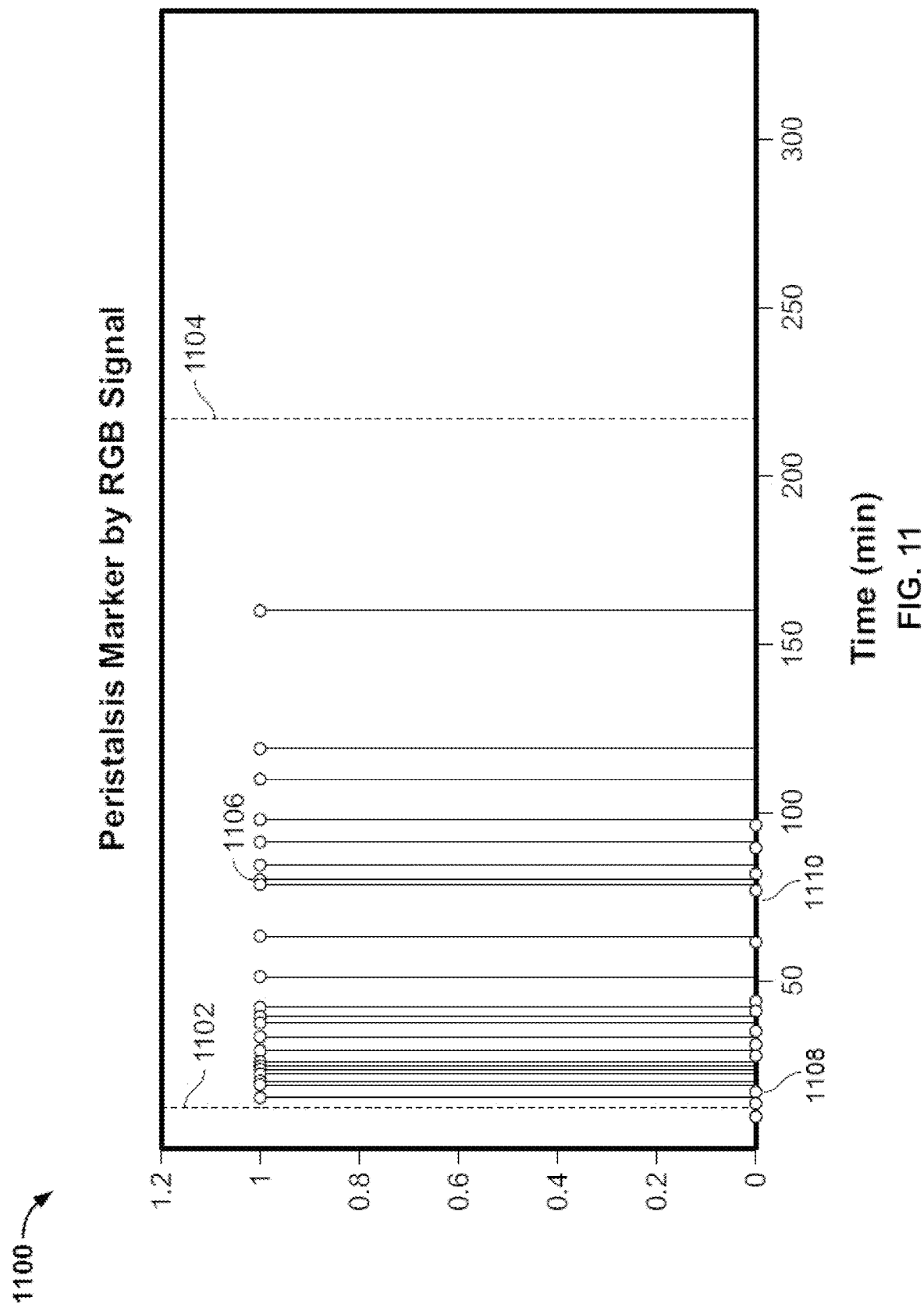
FIG. 11 is a plot illustrating muscle contractions detected by an ingestible device over time, which may be used when determining a location of an ingestible device as it transits through a GI tract, in accordance with some embodiments of the disclosure.

FIG. 11 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 100 may be configured to detect muscle contractions, and store data indicative of when each muscle contraction is detected (e.g., as part of 914 of process 900 (FIG. 9)). Plot 1100 depicts the detected muscle contractions 1106 over time, with each muscle contraction being represented by a vertical line reaching from "0" to "1" on the y-axis.

At 1102, around the 10-minute mark, ingestible device 100 first enters the duodenum (e.g., as determined by ingestible device 100 performing process 600 (FIG. 6)). Shortly thereafter, at 1108, ingestible device 100 begins to detect several muscle contractions 1106 in quick succession, which may be indicative of the strong peristaltic waves that form in the jejunum (e.g., jejunum 314 (FIG. 3)). Later, around 1110, ingestible device 100 continues to detect intermittent muscle contractions, which may be consistent with an ingestible device 100 within the ileum. Finally at 1104, ingestible device 100 transitions out of the small intestine, and into the cecum. Notably, ingestible device 100 detects more frequent muscle contractions in the jejunum portion of the small intestine as compared to the ileum portion of the small intestine, and ingestible device 100 does not measure any muscle contractions after having exited the small intestine. In some embodiments, ingestible device 100 may incorporate this information into a localization process. For example, ingestible device 100 may be configured to detect a transition from a jejunum to an ileum in response to determining that a frequency of detected muscle contractions (e.g., the number of muscle contractions measured in a given 10-minute window) has fallen below a threshold number. As another example, ingestible device 100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

Figure 12:
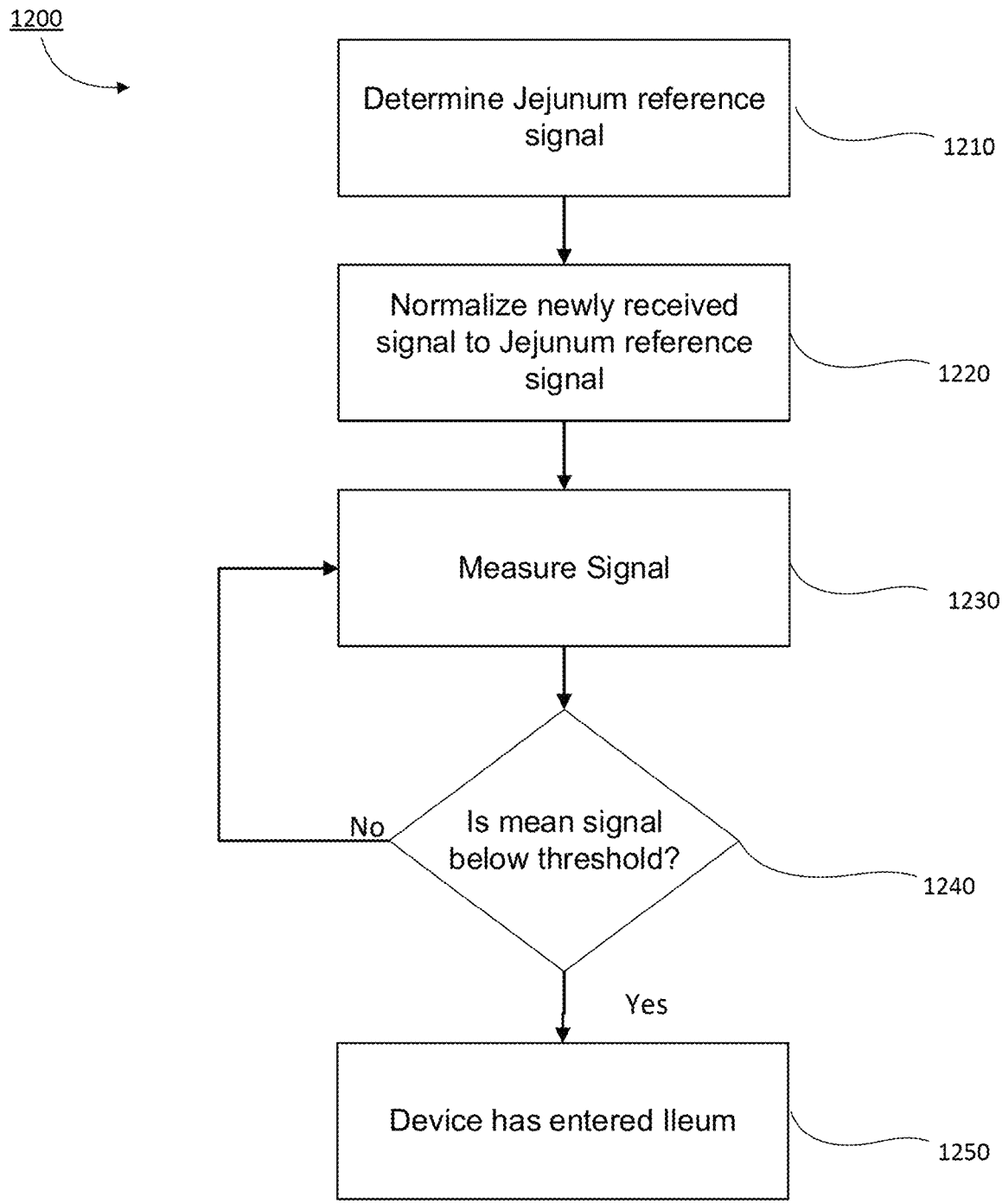
FIG. 12 is a flowchart of illustrative steps for detecting a transition from a jejunum to an ileum, which may be used when determining a location of an ingestible device as it transits through a GI tract, in accordance with some embodiments of the disclosure.

FIG. 12 is a flowchart 1200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more messentary fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 1200 represents a single sliding window process. In step 1210, the jejenum reference signal is determined based on optical reflection. Typically, this signal is as the average signal (e.g., reflected red light) over a period of time since the device was determined to enter the jejenum. The period of time can be, for example, from five minutes to 40 minutes (e.g., from 10 minutes to 30 minutes, from 15 minutes to 25 minutes). In step 1220, the detected signal (e.g., reflected red light) just after the period of time used in step 1210 is normalized to the reference signal determined in step 1210. In step 1230, the signal (e.g., reflected red light) is detected. In step 1240, the mean signal detected based on the single sliding window is compared to a signal threshold. The signal threshold in step 1240 is generally a fraction of the reference signal of the jejenum reference signal determined in step 1210. For example, the signal threshold can be from 60% to 90% (e.g., from 70% to 80%) of the jejenum reference signal. If the mean signal exceeds the signal threshold, then the process determines that the device has entered the ileum at step 1250. If the mean signal does not exceed the signal threshold, then the process returns to step 1230.

Figure 13:
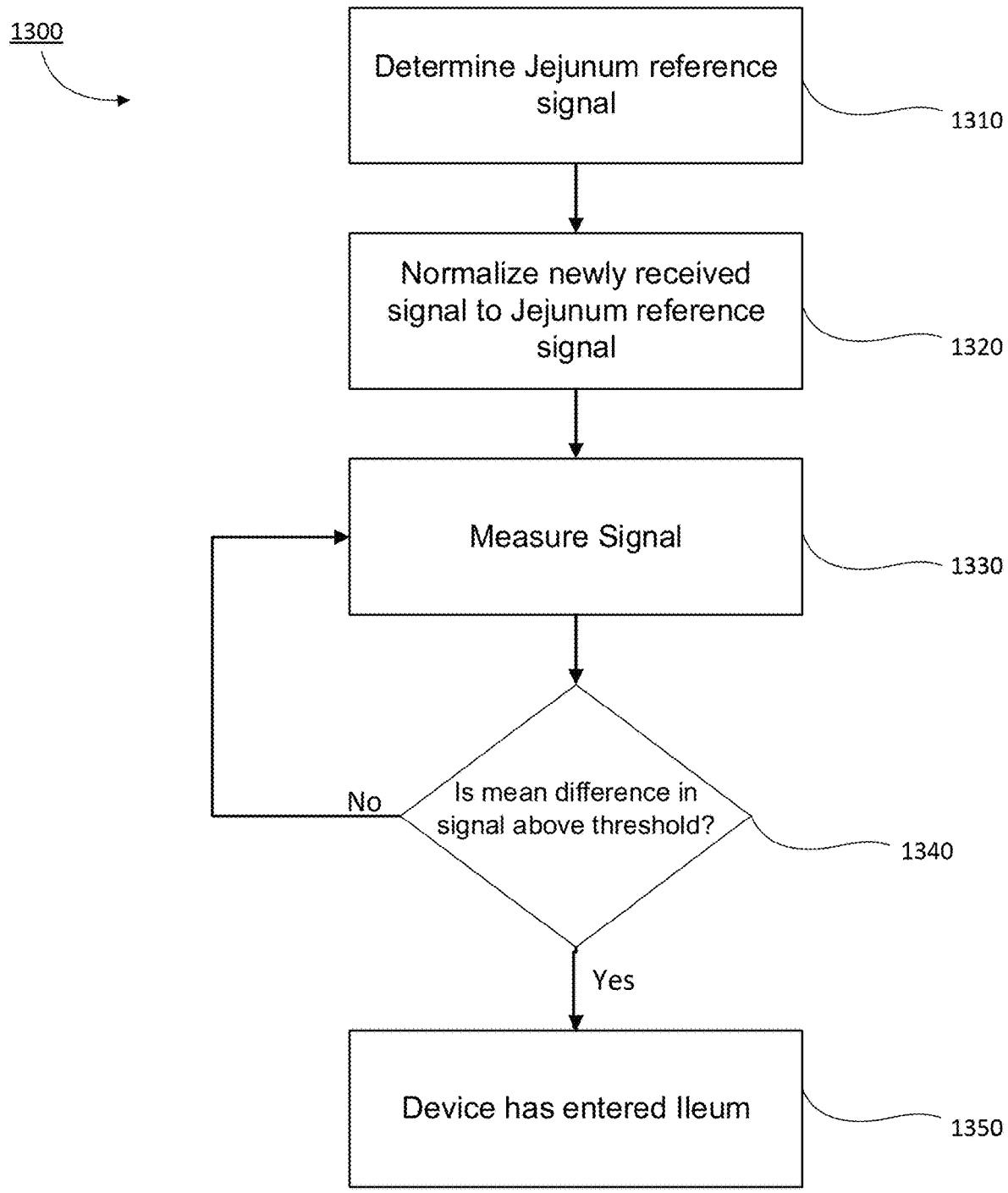
FIG. 13 is a flowchart of illustrative steps for detecting a transition from a jejunum to an ileum, which may be used when determining a location of an ingestible device as it transits through a GI tract, in accordance with some embodiments of the disclosure.

FIG. 13 is a flowchart 1200 for certain embodiments for determining a transition of the device from the jejunum to the ileum using a two sliding window process. In step 1310, the jejenum reference signal is determined based on optical reflection. Typically, this signal is as the average signal (e.g., reflected red light) over a period of time since the device was determined to enter the jejenum. The period of time can be, for example, from five minutes to 40 minutes (e.g., from 10 minutes to 30 minutes, from 15 minutes to 25 minutes). In step 1320, the detected signal (e.g., reflected red light) just after the period of time used in step 1310 is normalized to the reference signal determined in step 1310. In step 1330, the signal (e.g., reflected red light) is detected. In step 1340, the mean difference in the signal detected based on the two sliding windows is compared to a signal threshold. The signal threshold in step 1340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 1350. If the signal threshold is not exceeded, then the process returns to step 1330.

Figure 14:
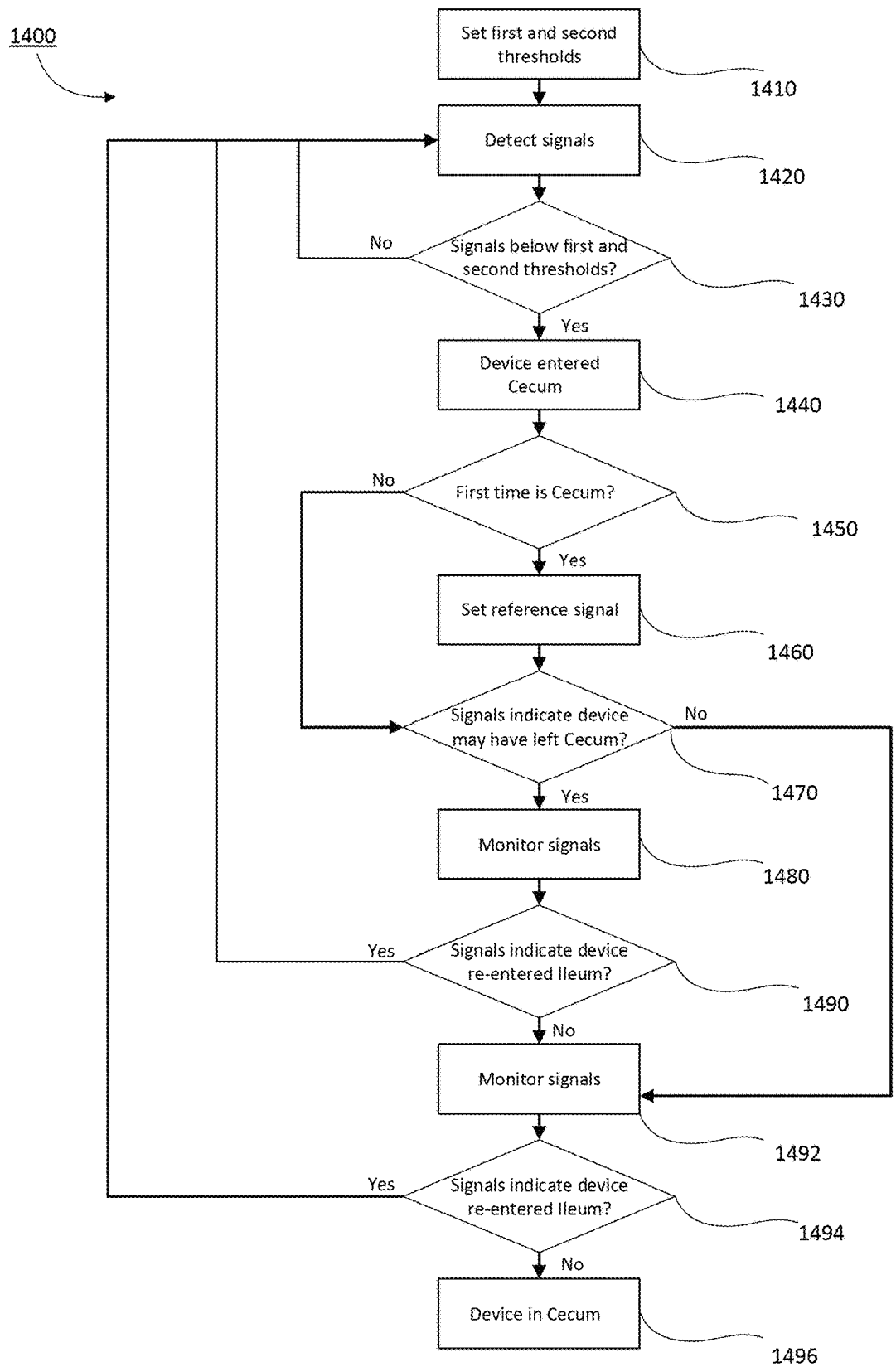
FIG. 14 is a flowchart of illustrative steps for detecting a transition from an ileum to a cecum, which may be used when determining a location of an ingestible device as it transits through a GI tract, in accordance with some embodiments of the disclosure.

FIG. 14 is a flowchart 1400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 1400, the sliding window analysis (first and second windows) discussed with respect to process 600 is continued.

Step 1410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 1420 includes detecting the signals in the first and second windows that are to be used for comparing to the first and second thresholds.

Step 1430 includes comparing the detected signals to the first and second thresholds. If the corresponding value is not below the first threshold or the corresponding value is not below the second threshold, then it is determined that the device has not left the ileum and entered the cecum, and the process returns to step 1420. If the corresponding value is below the first threshold and the corresponding value is below the second threshold, then it is determined that the device has left the ileum and entered the cecum, and the proceeds to step 1440.

Step 1450 includes determining whether it is the first time that that the device was determined to leave the ileum and enter the cecum. If it is the first time that the device was determined to leave the ileum and enter the cecum, then the process proceeds to step 1460. If it is not the first time that the device has left the ileum and entered the cecum, then the process proceeds to step 1470.

Step 1460 includes setting a reference signal. In this step the optical signal (e.g., ratio of detected red light to detected green light) as a reference signal.

Step 1470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 1460) and the coefficient of variation for the corresponding detected signal (e.g., ratio of detected green light to detected blue light) exceeds the second threshold. If it is determined that the device may have left the cecum and returned to the ileum, the process proceeds to step 1480.

Step 1480 includes continuing to detect the relevant optical signals for a period of time (e.g., at least one minute, from five minutes to 15 minutes).

Step 1490 includes determining whether the signals determined in step 1480 indicate (using the methodology discussed in step 1470) that the device re-entered the ileum. If the signals indicate that the device re-entered the ileum, the process proceeds to step 1420. If the signals indicate that the device is in the cecum, the process proceeds to step 1492.

Step 1492 includes continuing to monitor the relevant optical signals for a period of time (e.g., at least 30 minutes, at least one hour, at least two hours).

Step 1494 includes determining whether the signals determined in step 1492 indicate (using the methodology discussed in step 1470) that the device re-entered the ileum. If the signals indicate that the device re-entered the ileum, the process proceeds to step 1420. If the signals indicate that the device is in the cecum, the process proceeds to step 1496.

At step 1496, the process determines that the device is in the cecum.

Figure 15:
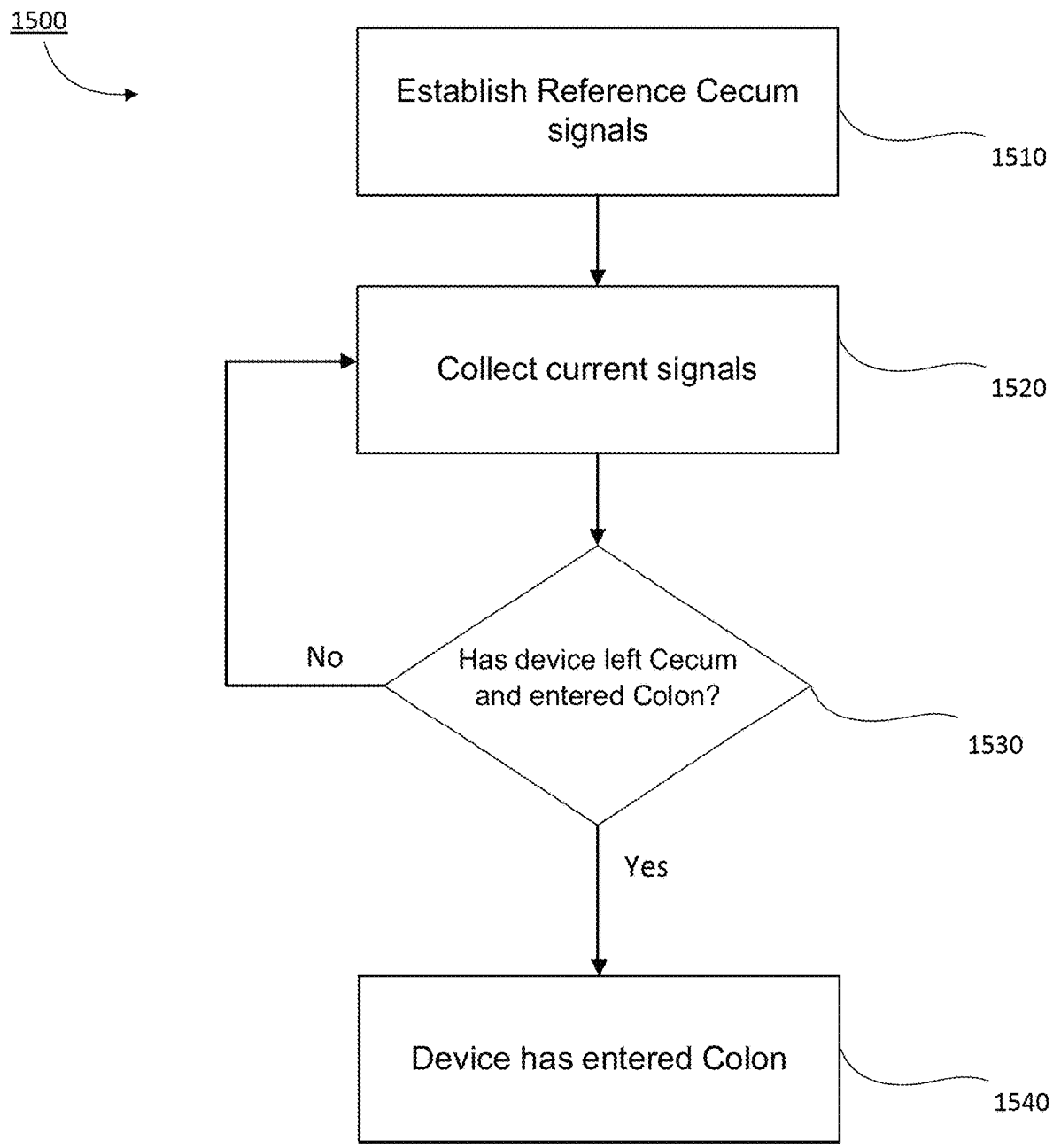
FIG. 15 is a flowchart of illustrative steps for detecting a transition from a cecum to a colon, which may be used when determining a location of an ingestible device as it transits through a GI tract, in accordance with some embodiments of the disclosure.

FIG. 15 is a flowchart 1500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 1500, the sliding window analysis (first and second windows) discussed with respect to process 1400 is continued.

In step 1510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 1480). The average values for the recorded optical signals (e.g., the ratio of reflected red signal to reflected green signal, and reflected blue signal) establish the cecum reference signals.

In step 1520, the optical signals are detected after it has been determined that the device entered the cecum (e.g., at step 1440). The optical signals are normalized to the cecum reference signals.

Step 1530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 1540. Otherwise, none of the three criteria are satisfied, the process returns to step 1520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 500 (FIG. 5), process 600 (FIG. 6), process 900 (FIG. 9), process 1200 (FIG. 12), process 1300 (FIG. 13), process 1400 (FIG. 14) and process 1500 (FIG. 15)). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 120 (FIG. 2)) may be written in a high-level procedural language such as object oriented programming, a scripting language or both. Accordingly, the program code may be written in C, C++ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

Figure 16:
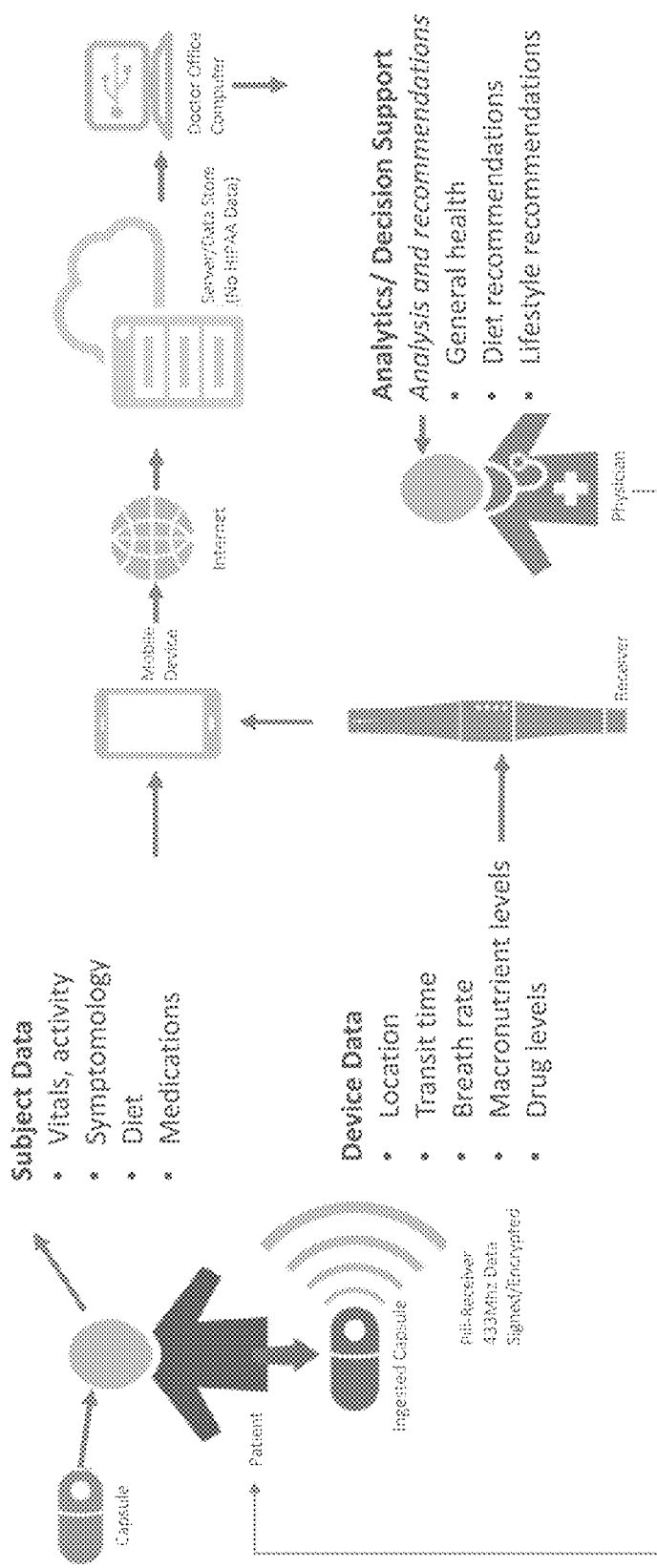
FIG. 16 illustrates an exemplary system for collecting, communicating and/or analyzing data about a subject.

FIG. 16 illustrates a nonlimiting example of a networked system for collecting, communicating and/or analyzing data about a subject, using an ingestible device as disclosed herein and one or more networked devices that communicate over one or more networks. For example, an ingestible device may be configured to communicate with an external base station. As an example, an ingestible device can have a communications unit that communicates with an external base station which itself has a communications unit. FIG. 16 illustrates exemplary implementation of such an ingestible device. As shown in FIG. 16, a subject ingests an ingestible device as disclosed herein. Certain data (which may be referred to as "device data") about the subject (e.g., based on a collected sample) and/or the location of the ingestible device in the GI tract of the subject are collected or otherwise available and provided to a mobile device, which then forwards the data via the internet and a server/data store to a physician's office computer. This collected data may also specify, for example, one or more of transit time, breath rate, one or more macronutrient levels and one or more drug levels. The data collected by the ingestible device is communicated (over one or more networks) to a receiver, such as, for example, a watch or other object worn by the subject. The data are then communicated from the receiver to the mobile device which then forwards or transmits (over one or more networks, such as the internet) the data and a server/data store/hardware storage device to a physician's office computer, or a data analytics system. The physician is then able to analyze some or all of the data about the subject to provide recommendations, such as, for example, general health recommendations, dietary health recommendations, decision support recommendations, and/or lifestyle recommendations. In some embodiments, the data analytics system retrieves the device data from the one or more hardware storage devices and processes (through execution of execution logic stored on the data analytics system) the device data to generate analytics data. While FIG. 16 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

Examples

An ingestible medical device according to the disclosure ("TLC1") was tested on 20 subjects to investigate its localization ability. TLC1 was a biocompatible polycarbonate capsule that contained a power supply, electronics and software. An onboard software algorithm used time, temperature and reflected light spectral data to determine the location of the capsule as it traveled the GI tract. The capsule is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the capsule was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:
1. Start mouth-esophagus transition detection after capsule is activated/administrated
2. Check whether Green <102.3 and Blue <94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green >110.1 or Blue >105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two minute gap between the front (first) and back (second) windows. The two minute gap was designed, at least in part, to skip the rapid transition from stomach to small intestine and capture the small intestine signal after capsule settles down in small intestine. The algorithm was as follows:
1. Start to check for stomach-duodenum transition after capsule enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the capsule has not gone back to stomach 2 hours after previously confirmed pyloric transition, stops location reversal monitoring and assume the capsule would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the capsule went back to stomach after first the first stomach-duodenum transition. The total agreement between the TLC1 algorithm detection and CT scans was 17/17=100%.

For one of the PillCam subjects, the capsule stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the G/B signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejenum Transition

For TLC1, it was assumed that the device left the duodenum and entered the jejenum three minutes after it was determined that the device entered the duodenum. Of the 17 subjects noted above with respect to the TLC1 investigation of the stomach-duodenum transition, 16 of the subjects mentioned had CT images that confirmed that the duodenum-jejenum transition was located somewhere between stomach and jejenum. One of the 17 subjects had a prolonged transit time in duodenum. The total agreement between algorithm detection and CT scans was 16/17=94%.

For PillCam, the duodenum-jejenum transition was not determined.

Jejenum-Ileum Transition

It is to be noted that the jejenum is redder and more vascular than ileum, and that the jejenum has a thicker intestine wall with more mesentery fat. These differences can cause various optical responses between jejenum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:
1. Obtain 20 minutes of Red signal after the duodenum jejenum transition, average the data and record it as the jejunum reference signal
2. Start to check the jejunum-ileum transition 20 minutes after the device enters the jejenum
   a. Normalize the newly received data by the jejenum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
1. Single-sliding-window analysis:
   a. 11 cases having jejunum-ileum transition detected somewhere between jejunum and cecum
   b. 24 cases having jejunum-ileum transition detected after cecum
   c. 19 cases having no jejunum-ileum transition detected
   d. Total agreement: 11/54=20%
2. Two-sliding-window analysis:
   a. 30 cases having jejunum-ileum transition detected somewhere between jejunum and cecum
   b. 24 cases having jejunum-ileum transition detected after cecum
   c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:
1. Start to monitor ileum-cecum transition after the capsule enters the stomach
2. Setup the two windows (front (first) and back (second))
   a. Use a five minute time length for each window
   b. Use a 10 minute gap between the two windows
   c. Use a one minute window sliding step size
3. Compare signals in the two sliding windows
   a. Set ileum-cecum transition flag if
      i. Reflected red/green has a significant change or is lower than a threshold
      ii. Coefficient of variation of reflected green/blue is lower than a threshold
   b. If this is the first ileum-cecum transition detected, record average reflected red/green signal in small intestine as small intestine reference signal
   c. Mark location reversal (i.e. capsule returns to terminal ileum) if
      i. Reflected red/green is statistically comparable with small intestine reference signal
      ii. Coefficient of variation of reflected green/blue is higher than a threshold
   d. If a possible ileum-cecum transition is detected, continue to scan for another 10 minutes for TLC1 (15 minutes for PillCam) in case of false positive flag
      i. If within this time frame (10 minutes for TLC1, 15 minutes for PillCam), location reversal is detected, the previous ileum-cecum transition flag is a false positive flag. Clear the flag and continue to check
      ii. If no location reversal has been identified within this time frame (10 minutes for TLC1, 15 minutes for PillCam) following the possible ileum-cecum transition flag, mark it as a confirmed ileum-cecum transition e. Continue monitoring data for another 2 hours after the confirmed ileum-cecum transition, in case of location reversal
   i. If a location reversal is identified, flag the timestamp when reversal happened and then repeat steps a-d to look for the next ileum-cecum transition
   ii. If the capsule has not gone back to small intestine 2 hours after previously confirmed ileum-cecum transition, stop location reversal monitoring and assume the capsule would stay in large intestinal area The flag setting and location reversal criteria particularly designed for TLC1 device were as follows:
1. Set ileum-cecum transition flag if
   a. The average reflected red/Green in the front window is less than 0.7 or mean difference between the two windows is higher than 0.6
   b. And the coefficient of variation of reflected green/blue is less than 0.02
2. Define as location reversal if
   a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
1. Good cases (39 subjects):
   a. For 31 subjects, the difference between the PillCam detection and the physician's notes was less than five minutes
   b. For 3 subjects, the difference between the PillCam detection and the physician's notes was less than 10 minutes
   c. For 5 subjects, the difference between the PillCam detection and the physician's notes was less than 20 minutes (the full transition can take up to 20 minutes before the signal settles)
2. Marginal/bad cases (13 subjects):
   a. Marginal cases (9 subjects)
      i. The PillCam ileum-cecum transition detection appeared in the terminal ileum or colon, but the difference between the two detections was within one hour
   b. Failed cases (4 subjects)
      i. Reasons of failure:
         1. The signal already stabilized in the terminal ileum
         2. The signal was highly variable from the entrance to exit
         3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected bluee provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after capsule enters cecum (The cecum-colon transition algorithm is dependent on the ileum-cecum transition flag)
   a. Normalize the newly received data by the cecum reference signals
   b. Two-sliding-window analysis:
      i. Use two adjacent 10 minute windows
      ii. Set the transition flag if any of the following criteria were met
         The mean difference in reflected red/green was more than 4× the standard deviation of reflected red/green in the back (second) window
         The mean of reflected red/green in the front (first) window was higher than 1.03
         The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.

The following table summarizes the localization accuracy results.

| Transition | TLC1 | PillCam |
| --- | --- | --- |
| Stomach-Duodenum | 100% (17/17) | 89% (48/54) |
| Duodenum-Jejenum | 94% (16/17) | N/A |
| Ileum-Cecum | 89% (16/18) | 75% (39/52) |

-continued

| Transition | TLC1 | PillCam |
|---|---|---|
| Ileum-terminal ileum/cecum/colon | 100% (18/18) | 92% (48/52) |

Other Embodiments

While the foregoing disclosure provides certain exemplary embodiments, the disclosure is not limited to such embodiments.

As an example, in some embodiments, a method may include a calibration step. The calibration step can be used to mitigate differences in results that at least partially result from differences in device design (e.g., relative location(s) of one or more light detectors relative to one or more light sources). Additionally or alternatively, calibration can involve using one or more mixtures that mimic one or more regions of the GI tract. Such calibration can be used to mitigate differences in results that at least partially result from differences in responsiveness/sensitivity of the light emission/detection system for one or more off the wavelengths of interest (e.g., red, green, blue). Information obtained via calibration can be used adjust data collected via the ingestible device when it is present in the GI tract.

As another example, while certain light sources have been disclosed, the disclosure is not limited to such light sources. Rather, any appropriate light source can be used. Exemplary light sources include OLEDs (e.g., active-matrix OLEDs), polymer LEDs, light emitting electrochemical cells (e.g., electroluminescent wires, fiber induced polymer electroluminescent light sources), chemiluminescent light sources, and lasers (e.g., diode lasers, solid state lasers, vertical cavity surface emitting lasers).

As a further example, while certain light detectors have been disclosed, the disclosure is not limited to such light detectors. Rather, any appropriate light source can be used. Exemplary light detectors include active pixel/CMOS sensors, CCDs, HgCdTe detectors, photodiodes, reverse-biased LEDs (acting as photodiodes), photoresistors (light dependent resistors), phototransistors, quantum dot photoconductors, quantum dot photodiodes, photovoltaic/solar cells, silicon photomultipliers, thermal detectors, and graphene/silicon photodetectors The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods.

Embodiments can be implemented in digital electronic circuitry, or in computer hardware, firmware, software, or in combinations thereof. Apparatus of the techniques described herein can be implemented in a computer program product tangibly embodied or stored in a machine-readable storage device for execution by a programmable processor; and method actions can be performed by a programmable processor executing a program of instructions to perform functions of the invention by operating on input data and generating output. The techniques can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

Various modifications and variations may be made to these example embodiments without departing from the spirit and scope of the embodiments, and the appended listing of embodiments should be given the broadest interpretation consistent with the description as a whole.

What is claimed is:

1. A method for determining a location of an ingestible device within a gastrointestinal tract of a body, the method comprising:
    transmitting a first illumination at a first wavelength and a second illumination at a second wavelength towards an environment external to a housing of the ingestible device;
    detecting a first reflectance from the environment resulting from the first illumination;
    detecting a second reflectance from the environment resulting from the second illumination, wherein the first reflectance value is indicative of an amount of light in the first reflectance, and the second reflectance value is indicative of an amount of light in the second reflectance;
    storing on the ingestible device, a ratio of the first reflectance value and the second reflectance value in a data set, the data set including a plurality of values, each of the plurality of values corresponding to a respective ratio of a respective first reflectance and a respective second reflectance detected at a respective time;
    obtaining, from the data set, a first subset of values, the first subset of values corresponding to a first predetermined number of recent measurements;
    obtaining, from the data set, a second subset of values, the second subset of values corresponding to a second predetermined number of past measurements, the recent measurements being taken at a recent time range that is separated from a past time range when the past measurements were taken by at least a predetermined period of time; and
    detecting by the ingestible device a transition in the location of the ingestible device between two different sequential portions of the gastrointestinal tract of the body in response to a difference between a first mean value of the first subset of values and a second mean value of the second subset of values exceeding a threshold value.

2. The method of claim 1, wherein:
the first wavelength is in the green spectrum of light between 495-600 nm;
the second wavelength is in the blue spectrum of light between 400-495 nm; and
the first wavelength and the second wavelength are separated by at least 50 nm.

3. The method of claim 1, wherein obtaining the first subset of values and obtaining the second subset of values comprise:
obtaining a first raw subset of values by applying a first sliding window filter to the data set;
obtaining a second raw subset of values by applying a second sliding window filter to the data set;
determining the first subset of values by removing a first set of outliers from the first raw subset of values, the first set of outliers being identified based on a standard deviation of the first raw subset of values; and
determining the second subset of values by removing a second set of outliers from the second raw subset of values, the second set of outliers being identified based on a standard deviation of the second raw subset of values.

4. The method of claim 1, further comprising:
using a first detector to detect light at the first wavelength; and
using a second detector to detect light at the second wavelength, wherein the second detector is different from the first detector.

5. The method of claim 1, wherein the first wavelength is in the green spectrum of light between 495-600 nm.

6. The method of claim 5, wherein the second wavelength is in the blue spectrum of light between 400-495 nm.

7. The method of claim 1, wherein the first wavelength is in the blue spectrum of light between 400-495 nm.

8. The method of claim 1, wherein the first wavelength and the second wavelength are separated by at least 50 nm.

9. The method of claim 1, further comprising:
using a detector to detect light at the first wavelength; and
using the detector to detect light at the second wavelength.

10. The method of claim 1, wherein the threshold level is based on a standard deviation of at least one member selected from the group consisting of the first subset of values and the second subset of values.

11. The method of claim 1, wherein detecting the transition in the location of the ingestible device comprises identifying that the ingestible device moved from the stomach to the duodenum.

12. The method of claim 1, wherein detecting the transition in the location of the ingestible device comprises identifying that the ingestible device moved from the duodenum to the stomach.

13. The method of claim 1, wherein detecting the transition in the location of the ingestible device comprises determining that the ingestible device moved from the jejunum to the ileum.

14. The method of claim 1, wherein detecting the transition in the location of the ingestible device comprises determining that the ingestible device moved from the ileum to the cecum.

15. The method of claim 1, wherein detecting the transition in the location of the ingestible device comprises determining that the ingestible device moved from the cecum to the colon.

16. An ingestible device, comprising:
a housing;
one or more processing devices; and
one or more non-transitory machine readable hardware storage devices storing instructions that are executable by the one or more processing devices to perform operations comprising:
transmitting a first illumination at a first wavelength and a second illumination at a second wavelength towards an environment external to the housing;
detecting a first reflectance from the environment resulting from the first illumination;
detecting a second reflectance from the environment resulting from the second illumination, wherein the first reflectance value is indicative of an amount of light in the first reflectance, and the second reflectance value is indicative of an amount of light in the second reflectance;
storing a ratio of the first reflectance value and the second reflectance value in a data set, the data set including a plurality of values, each of the plurality of values corresponding to a respective ratio of a respective first reflectance and a respective second reflectance detected at a respective time;
obtaining, from the data set, a first subset of values, the first subset of values corresponding to a first predetermined number of recent measurements;
obtaining, from the data set, a second subset of values, the second subset of values corresponding to a second predetermined number of past measurements, the recent measurements being taken at a recent time range that is separated from a past time range when the past measurements were taken by at least a predetermined period of time; and
detecting by the ingestible device a transition in the location of the ingestible device between two different sequential portions of the gastrointestinal tract of the body in response to a difference between a first mean value of the first subset of values and a second mean value of the second subset of values exceeding a threshold value.

17. The ingestible device of claim 16, further comprising first and second light sources, wherein the first light source is configured to emit light at the first wavelength, and the second light source is configured to emit light at the second wavelength different.

18. The ingestible device of claim 17, further comprising a detector configured to detect light at the first and second wavelengths.

19. The ingestible device of claim 17, further comprising first and second detectors, wherein the first detector is configured to detect light at the first wavelength, and the second detector is configured to detect light at the second wavelength.

20. The ingestible device of claim 16, wherein obtaining the first subset of values and obtaining the second subset of values comprise:
obtaining a first raw subset of values by applying a first sliding window filter to the data set;
obtaining a second raw subset of values by applying a second sliding window filter to the data set;
determining the first subset of values by removing a first set of outliers from the first raw subset of values, the first set of outliers being identified based on a standard deviation of the first raw subset of values; and determining the second subset of values by removing a second set of outliers from the second raw subset of values, the second set of outliers being identified based on a standard deviation of the second raw subset of values.

21. The ingestible device of claim 16, wherein the first wavelength is in the green spectrum of light between 495-600 nm.

22. The ingestible device of claim 21, wherein the second wavelength is in the blue spectrum of light between 400-495 nm.

23. The ingestible device of claim 22, wherein the first wavelength and the second wavelength are separated by at least 50 nm.

24. The ingestible device of claim 16, wherein the first wavelength is in the blue spectrum of light between 400-495 nm.

25. The ingestible device of claim 16, wherein the first wavelength and the second wavelength are separated by at least 50 nm.

26. The ingestible device of claim 16, wherein the threshold level is based on a standard deviation of at least one member selected from the group consisting of the first subset of values and the second subset of values.

27. The ingestible device of claim 16, wherein detecting the transition in the location of the ingestible device comprises identifying that the ingestible device moved from the stomach to the duodenum.

28. The ingestible device of claim 16, wherein detecting the transition in the location of the ingestible device comprises identifying that the ingestible device moved from the duodenum to the stomach.

29. The ingestible device of claim 16, wherein detecting the transition in the location of the ingestible device comprises determining that the ingestible device moved from the jejunum to the ileum.

30. The ingestible device of claim 16, wherein detecting the transition in the location of the ingestible device comprises determining that the ingestible device moved from the ileum to the cecum.

31. The ingestible device of claim 16, wherein detecting the transition in the location of the ingestible device comprises determining that the ingestible device moved from the cecum to the colon.

* * * * *